(12) United States Patent
Pan et al.

(10) Patent No.: US 10,358,444 B2
(45) Date of Patent: *Jul. 23, 2019

(54) UNSYMMETRICAL BENZOTHIADIAZOLE-BASED MOLECULAR COMPLEXES

(71) Applicant: PHILLIPS 66 COMPANY, Houston, TX (US)

(72) Inventors: Hualong Pan, Bartlesville, OK (US); Kathy Woody, Bartlesville, OK (US); Brian Worfolk, Bartlesville, OK (US); Taeshik Earmme, Bartlesville, OK (US)

(73) Assignee: PHILLIPS 66 COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/644,186

(22) Filed: Jul. 7, 2017

(65) Prior Publication Data

US 2018/0022718 A1 Jan. 25, 2018

Related U.S. Application Data

(60) Provisional application No. 62/364,088, filed on Jul. 19, 2016.

(51) Int. Cl.
| C07D 417/14 | (2006.01) |
| C07D 285/14 | (2006.01) |
| H01L 51/00 | (2006.01) |
| H01L 51/42 | (2006.01) |

(52) U.S. Cl.
CPC ......... C07D 417/14 (2013.01); C07D 285/14 (2013.01); H01L 51/0036 (2013.01); H01L 51/0047 (2013.01); H01L 51/4253 (2013.01); Y02E 10/549 (2013.01)

(58) Field of Classification Search
CPC .................................................. C07D 417/14
See application file for complete search history.

(56) References Cited

U.S. PATENT DOCUMENTS

| 8,334,456 | B2* | 12/2012 | Zhu | B82Y 10/00 136/263 |
| 8,723,028 | B2* | 5/2014 | Zhu | H01L 51/0043 136/263 |
| 8,748,739 | B2* | 6/2014 | Zhu | B82Y 10/00 136/263 |
| 8,772,442 | B2* | 7/2014 | Zhu | H01L 51/0043 136/263 |
| 9,908,857 | B2* | 3/2018 | Pan | C07D 285/14 |
| 2010/0307594 | A1* | 12/2010 | Zhu | B82Y 10/00 136/263 |
| 2014/0073753 | A1* | 3/2014 | Seferos | C08G 61/126 526/172 |

FOREIGN PATENT DOCUMENTS

CN 105713185 A * 6/2016

OTHER PUBLICATIONS

Li et al. Bul.. Korean Chem. Soc. 2014, 35, 505-512 (Year: 2014).*
Wang et al. Chin. J. Chem. 2013, 31, 1367-1379 (Year: 2013).*

* cited by examiner

Primary Examiner — Matthew P Coughlin
(74) Attorney, Agent, or Firm — Phillips 66 Company

(57) ABSTRACT

A molecular complex comprising

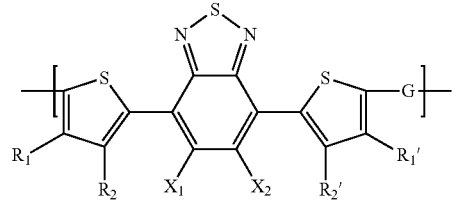

wherein X1 and X2 are independently selected from the group consisting of: H, Cl, F, CN, alkyl, alkoxy, ester, ketone, amide and aryl groups; R1, R2, R1' and R2' are side chains independently selected from the group consisting of: H, Cl, F, CN, alkyl, alkoxy, alkylthio, ester, ketone and aryl groups; G is an aryl group; and wherein the thiophene groups are unsymmetrical.

8 Claims, 22 Drawing Sheets

UNSYMMETRICAL BENZOTHIADIAZOLE-BASED MOLECULAR COMPLEXES

CROSS-REFERENCE TO RELATED APPLICATIONS

This application is a non-provisional application which claims the benefit of and priority to U.S. Provisional Application Ser. No. 62/364,088 filed Jul. 19, 2016, entitled "Unsymmetrical Benzothiadiazole-Based Molecular Complexes," which is hereby incorporated by reference in its entirety.

STATEMENT REGARDING FEDERALLY SPONSORED RESEARCH OR DEVELOPMENT

None.

FIELD OF THE INVENTION

This invention relates to unsymmetrically substituted benzothiadiazole-based molecular complexes.

BACKGROUND OF THE INVENTION

Solar energy using photovoltaic effect requires active semiconducting materials to convert light into electricity. Currently, solar cells based on silicon are the dominating technology due to their high conversion efficiency. Recently, solar cells based on organic materials showed interesting features, especially on the potential of low cost in materials and processing. Judging from the recent success in organic light emitting diodes based on a reverse effect of photovoltaic effect, organic solar cells are very promising.

Organic photovoltaic cells have many potential advantages when compared to traditional silicon-based devices. Organic photovoltaic cells are light weight, economical in the materials used, and can be deposited on low cost substrates, such as flexible plastic foils. However, organic photovoltaic devices typically have relatively low power conversion efficiency (the ratio of incident photons to energy generated). This is, in part, thought to be due to the morphology of the active layer. The charge carriers generated must migrate to their respective electrodes before recombination or quenching occurs. The diffusion length of an exciton is typically much less than the optical absorption length, requiring a tradeoff between using a thick, and therefore resistive, cell with multiple or highly folded interfaces, or a thin cell with a low optical absorption efficiency.

Conjugated polymers are polymers containing π-electron conjugated units along the main chain. They can be used as active layer materials for some types of photo-electric devices, such as polymer light emitting devices, polymer solar cells, polymer field effect transistors, etc. As polymer solar cell materials, conjugated polymers should possess some properties, such as high charge carrier mobility, good harvest of sunlight, good processability, and proper molecular energy levels. Some conjugated polymers have proven to be good solar cell materials. Conjugated polymers are made of alternating single and double covalent bonds. The conjugated polymers have a δ-bond backbone of intersecting $sp^2$ hybrid orbitals. The $p_z$ orbitals on the carbon atoms overlap with neighboring $p_z$ orbitals to provide π-bonds. The electrons that comprise the π-bonds are delocalized over the whole molecule. The semiconducting properties of the photovoltaic polymers are derived from their delocalized π bonds. The substituents of the polymers also largely influence the electronic properties. The optical bandgap, mobility and thin-film morphology are affected by both the type of functional group used as a substituent and the bulkiness and length of the side chain. Polymers which have only minor differences in the side chains will have large differences in the device performance.

There is a need in the art for polymer solar cells that exhibit increased power conversion efficiency and fill factor.

BRIEF SUMMARY OF THE DISCLOSURE

A molecular complex comprising

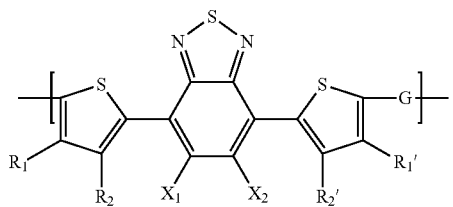

wherein X1 and X2 are independently selected from the group consisting of: H, Cl, F, CN, alkyl, alkoxy, ester, ketone, amide and aryl groups; R1, R2, R1' and R2' are side chains independently selected from the group consisting of: H, Cl, F, CN, alkyl, alkoxy, alkylthio, ester, ketone and aryl groups; G is an aryl group; and wherein the thiophene groups are unsymmetrical.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
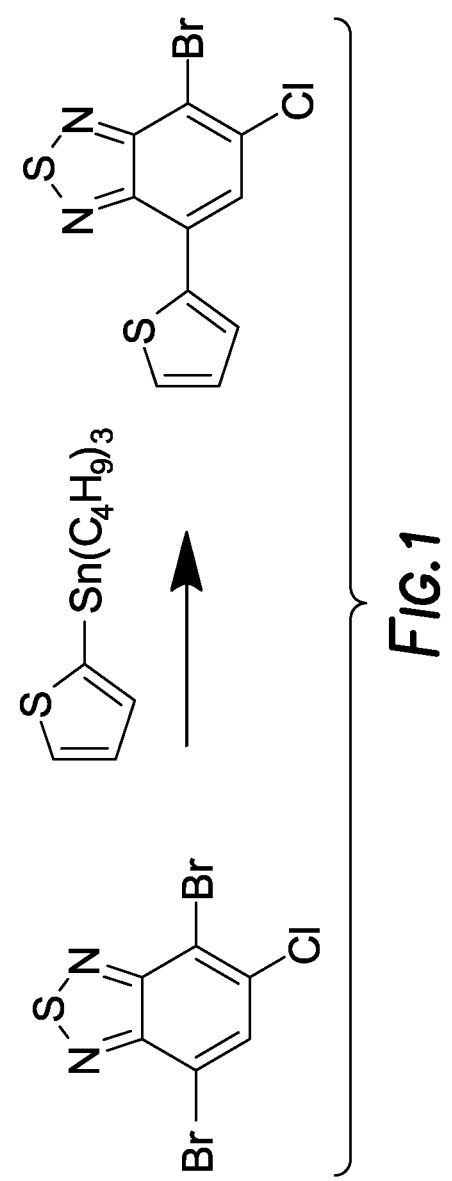
FIG. 1, depicts the reaction of 4,7-Dibromo-5-chloro-2,1,3-benzothiadiazole and tributyl(thiophen-2-yl)stannane to produce 4-bromo-5-chloro-7-(thiophen-2-yl)benzo[c][1,2,5]thiadiazole.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

"Alkyl," as used herein, refers to an aliphatic hydrocarbon chains. In one embodiment the aliphatic hydrocarbon chains are of 1 to about 100 carbon atoms, preferably 1 to 30 carbon atoms, and includes straight and branched chained, single, double and triple bonded carbons such as methyl, ethyl, n-propyl, isopropyl, n-butyl, isobutyl, sec-butyl, t-butyl, n-pentyl, isopentyl, neo-pentyl, n-hexyl, isohexyl, thenyl, propenyl, butenyl, pentenyl, hexenyl, butadienyl, pentadienyl, hexadienyl, ethynyl, propynyl, butynyl, pentynyl, hexynyl, 2-ethylhexyl, 2-butyloctyl, 2-hexyldecyl, 2-octyldedodecyl, 2-decyltetradecy and the like. In this application alkyl groups can include the possibility of substituted and unsubstituted alkyl groups. Substituted alkyl groups can include one or more halogen substituents.

"Alkoxy," as used herein, refers to the group R—O— where R is an alkyl group of 1 to 100 carbon atoms. Examples of alkoxy groups include, but are not limited to, methoxy, ethoxy, propoxy (e.g., n-propoxy and isopropoxy), t-butoxy, pentoxyl, hexoxyl groups, and the like. In this application alkoxy groups can include the possibility of substituted and unsubstituted alkoxy groups.

"Alkylthio" as used herein refers to an —S— alkyl group. Examples of alkylthio groups include, but are not limited to, methylthio, ethylthio, propylthio (e.g., n-propylthio and isopropylthio), t-butylthio, pentylthio, hexylthio groups, and the like. In this application alkylthio groups can include the possibility of substituted and unsubstituted alkylthio groups.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, phenanthrenyl, pentacenyl, cyclopentane, cyclohexane, imidazoline, pyran, benzodioxanyl, benzodioxolyl, chromanyl, indolinyl, and the like. Aryl groups can be optionally substituted with one or with one or more Rx. In this application aryl groups can include the possibility of substituted aryl groups (such as heteroaryls), bridged aryl groups and fused aryl groups.

Fill Factor (FF) as used herein, is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation: $FF=(V_{mp}*J_{mp})/(J_{sc}*V_{oc})$ where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells.

Open-circuit voltage ($V_{oc}$) as used herein is the difference in the electrical potentials between the anode and the cathode of a device when there is no external load connected.

Power conversion efficiency as used herein, of a solar cell is the percentage of power converted from absorbed light to electrical energy. The power conversion efficiency of a solar cell can be calculated by dividing the maximum power point ($P_m$) by the input light irradiance (E, in $W/m^2$) under standard test conditions and the surface area of the solar cell ($A_c$ in $m^2$). standard test conditions typically refers to a temperature of 25° C. and an irradiance of 1000 $W/m^2$ with an air mass 1.5 (AM 1.5G) spectrum.

The present application relates to polymeric compounds that can be used as organic semiconductor materials. The present compounds can have good solubility in various common solvents and good stability in air. When incorporated into optical or optoelectronic devices including, but not limited to, photovoltaic or solar cells, light emitting diodes, and light emitting transistors, the present compounds can confer various desirable performance properties. For example, when the present compounds are used in a photoactive layer of a solar cell (e.g., bulk heterojunction devices), the solar cell can exhibit very high power conversion efficiency (e.g., about 7.0% or greater) and very high fill factor (e.g., about 68% or greater).

The present embodiment describes a molecular complex comprising

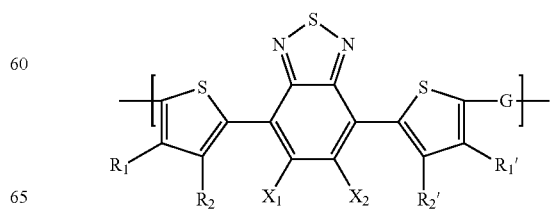

wherein: X1 and X2 are independently selected from the group consisting of: H, Cl, F, CN, alkyl, alkoxy, ester, ketone, amide and aryl groups; R1, R2, R1' and R2' are side chains independently selected from the group consisting of: H, Cl, F, CN, alkyl, alkoxy, alkylthio, ester, ketone and aryl groups; G is an aryl group; and wherein the thiophene groups are unsymmetrical.

The aryl group G can be selected from groups such as a benzodithiophenyl group, a silylene-bithiophenyl group, a carbazolyl group, and a dibenzosilole group, each of which can be optionally substituted as described herein. For example, the benzodithiophenyl group, the silylene-bithiophenyl group, the carbazolyl group, and the dibenzosilole group can be substituted with one, two, three or four solubilizing groups. Each solubilizing group can be a linear or branched aliphatic group (e.g., an alkyl group, an alkenyl group, an alkoxy group, or an alkylthio group) having 6-20 carbon atoms. In particular embodiments, each solubilizing group can be a branched C6-20 alkyl group or a branch C6-20 alkoxy group. Other examples of aryl groups such as polycyclic hetroaryl groups of G can include:

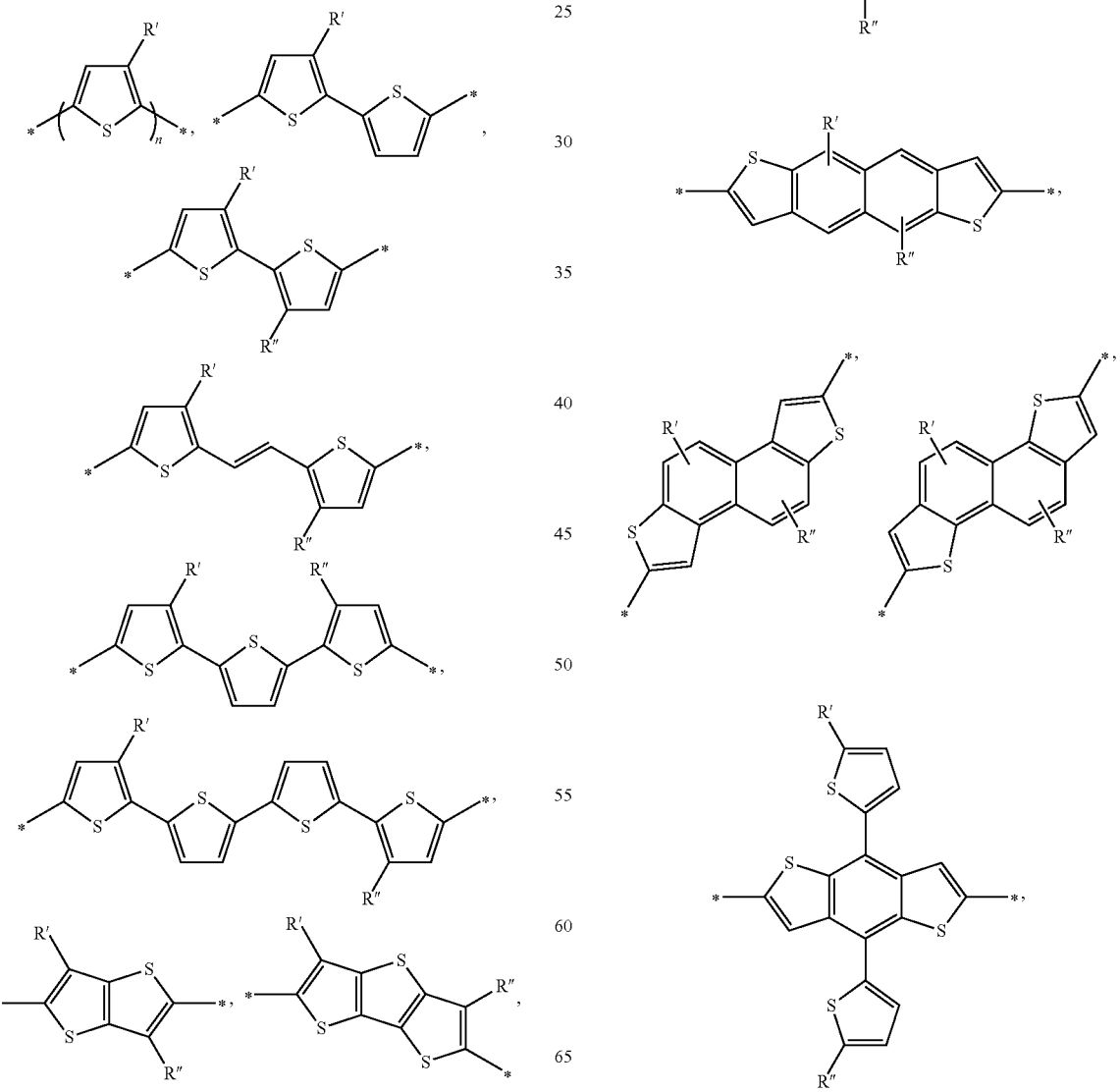

-continued

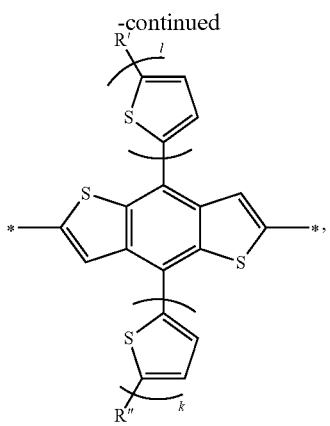

In the above examples W can be C, Si or Se. R', R" can be independently selected from H, Cl, F, CN, an alkyl group, an alkoxy group, an aryl group, a $C_{6-20}$ alkyl group, a —O—$C_{6-20}$ alkyl group, a —O—$_{C6-20}$ alkenyl group, a —O—$C_{6-20}$ haloalkyl group, a —S—$C_{6-20}$ alkyl group, a —S—$C_{6-20}$ alkenyl group, a —S—$C_{6-20}$ haloalkyl group, a-thienyl-$C_{6-20}$ alkyl group, a-thienyl-$C_{6-20}$ alkenyl group, and a-thienyl-$C_{6-20}$ haloalkyl group The formation of the molecular complex of coupling G can be performed by any conventionally known coupling reaction. Examples of different coupling reactions that can be used include, Wurtz reaction, Glaser coupling, Ullman reaction, Gomberg-Bachmann reaction, Cadiot-Chodkiewicz coupling, Pinacol coupling reaction, Castro-Stephens coupling, Gilman reagent coupling, Cassar reaction, Kumada coupling, Heck reaction, Sonogashira coupling, Negishi coupling, Stile coupling, Suzuki reaction, Hiyama coupling, Buchwald-Hartwig reaction, Fukuyama coupling, Liebeskind-Srogl coupling, Direct Heteroarylation and MacMillan coupling.

The unsymmetrical thiophene group can mean a variety of combinations such as R1 and R1' not being identical, R2 and R2' not being identical or both R1 and R1' and R2 and R2' not being identical.

It is theorized that the unsymmetrical thiophene groups contribute to increased power conversion efficiency and increased fill factor. When compared to symmetric thiophene groups such as those found in U.S. Pat. No. 8,723,028, the unsymmetric sidechain polymer outperformed in short circuit current, fill factor percentage and power conversion efficiency percentage. In one embodiment, the unsymmetric thiophene groups can produce fill factor percentages of at least 69%, 70%, 71%, 72%, 73%, or even 74%. In one embodiment, the unsymmetric thiophene groups can produce power conversion efficiencies of at least 7%, 7.1%, 7.2%, 7.3%, 7.4%, 7.6%, or even 7.8%.

The polymers or oligomers produced from the present disclosure can be used as part of a photovoltaic material or an active layer material in a photovoltaic device or an electronic device such as photodetector devices, solar cell devices, and the like. Photovoltaic devices, including solar cell devices, are generally comprised of laminates of a suitable photovoltaic material between a hole-collecting electrode layer and an electron-collecting layer. Additional layers, elements or a substrate may or may not be present. In one embodiment the electronic devices are field effect transistors, light emitting devices, and sensors, electrochromic devices and capacitors.

In one embodiment the molecular complex is used a polymer or oligomer for organic photovoltaic devices. In this embodiment the organic photovoltaic device comprises a cathode, disposed over an electron transport layer, disposed above a polymer or oligomer created from the molecular complex of the present teachings, disposed above an anode. In this embodiment the polymer the electron transport layer can comprise $(AO_x)_{yy}BO_{(1-y)}$ with an optional fullerene dopant.

The anode for the organic photovoltaic device can be any conventionally known anode capable of operating as an organic photovoltaic device. Examples of anodes that can be used include: indium tin oxide (ITO), fluorine doped tin oxide (FTO), aluminum, silver, gold, carbon, carbon nanotubes, graphite, graphene, PEDOT:PSS, copper, metal nanowires or meshes, $Zn_{99}InO_x$, $Zn_{98}In_2O_x$, $Zn_{97}In_3O_x$, $Zn_{95}Mg_5O_x$, $Zn_{90}Mg_{10}O_x$, and $Zn_{85}Mg_{15}O_x$.

The cathode for the organic photovoltaic device can be any conventionally known cathode capable of operating as an organic photovoltaic device. Examples of cathodes that can be used include: indium tin oxide, carbon, graphite, graphene, PEDOT:PSS, copper, silver, gold, aluminum, metal nanowires.

The electron transport layer of the organic photovoltaic device comprises $(AO_x)_yBO_{(1-y)}$. In this embodiment, $(AO_x)_y$ and $BO_{(1-y)}$ are metal oxides. A and B can be different metals selected to achieve ideal electron transport layers.

In one embodiment A can be aluminum, indium, zinc, tin, copper, nickel, cobalt, iron, ruthenium, rhodium, osmium, tungsten, magnesium, indium, vanadium, titanium and molybdenum.

In one embodiment B can be aluminum, indium, zinc, tin, copper, nickel, cobalt, iron, ruthenium, rhodium, osmium, tungsten, vanadium, titanium and molybdenum.

Examples of $(AO_x)_yBO_{(1-y)}$ include: $(SnO_x)_yZnO_{(1-y)}$, $(AlO_x)_yZnO_{(1-y)}$, $(AlO_x)_yInO_{z(1-y)}$, $(AlO_x)_ySnO_{z(1-y)}$, $(AlO_x)_yCuO_{z(1-y)}$, $(AlO_x)_yWO_{z(1-y)}$, $(InO_x)_yZnO_{(1-y)}$, $(InO_x)_ySnO_{z(1-y)}$, $(InO_x)_yNiO_{z(1-y)}$, $(ZnO_x)_yCuO_{z(1-y)}$, $(ZnO_x)_yNiO_{z(1-y)}$, $(ZnO_x)_yFeO_{z(1-y)}$, $(WO_x)_yVO_{z(1-y)}$, $(WO_x)_yTiO_{z(1-y)}$, and $(WO_x)_yMoO_{z(1-y)}$.

In one embodiment, $(AO_x)_yBO_{(1-y)}$ contains from about 10% to about 25% atomic % of acetate as characterized with x-ray photoelectron spectroscopy.

In one embodiment, the production of $(AO_x)_yBO_{(1-y)}$ occurs from reacting an organic A precursor in the amounts of (1-y); an organic B precursor in the amounts of y; and a base in the amount of (1-y) to 1.

Examples of fullerene dopants that can be combined with the electron transport layer include

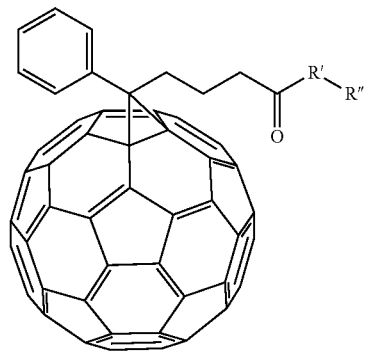

and [6,6]-phenyl-$C_{60}$-butyric-N-2-trimethylammonium ethyl ester iodide.

In the embodiment of

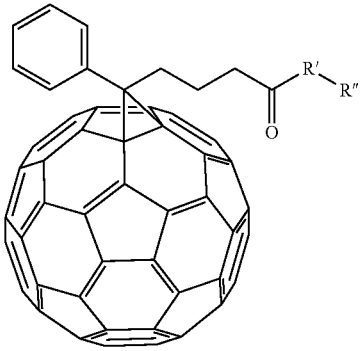

R' can be selected from either N, O, S, C, or B. In other embodiment R" can be alkyl chains or substituted alkyl chains. Examples of substitutions for the substituted alkyl chains include halogens, N, Br, O, Si, or S. In one example R" can be selected from

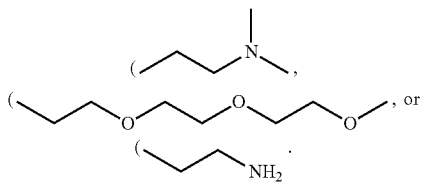

Other examples of fullerene dopants that can be used include: [6,6]-phenyl-$C_{60}$-butyric-N-(2-aminoethyl)acetamide, [6,6]-phenyl-$C_{60}$-butyric-N-triethyleneglycol ester and [6,6]-phenyl-$C_{60}$-butyric-N-2-dimethylaminoethyl ester.

Representative Molecular Complex Synthesis.

Figure 2:
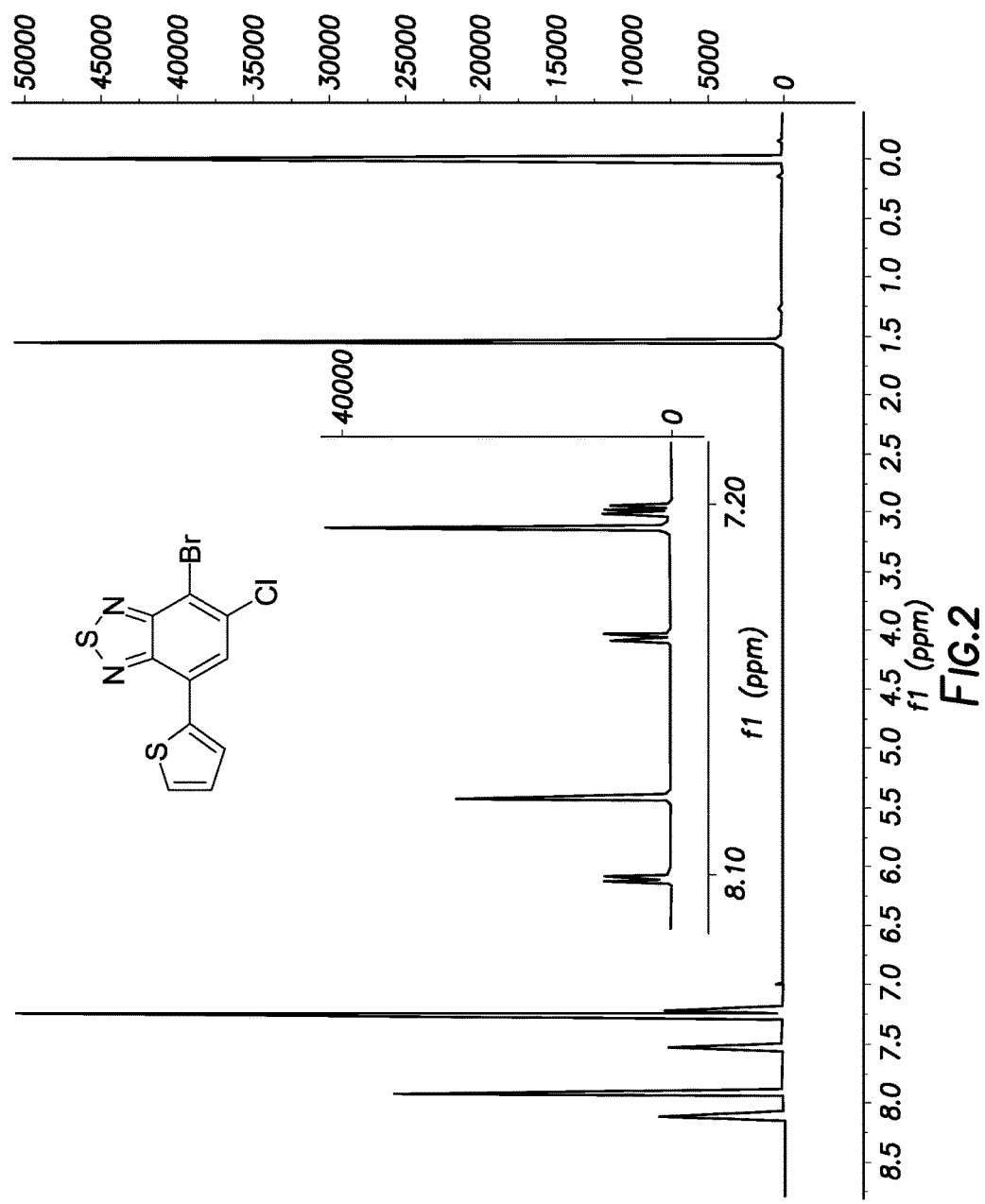
FIG. 2, depicts the NMR of 4-bromo-5-chloro-7-(thiophen-2-yl)benzo[c][1,2,5]thiadiazole.

The first step involves the synthesis of 4-bromo-5-chloro-7-(thiophen-2-yl)benzo[c][1,2,5]thiadiazole. 4,7-Dibromo-5-chloro-2,1,3-benzothiadiazole (2.2 g, 0.007 mol), tributyl (thiophen-2-yl)stannane (2.5 g, 0.007 mol), and tetrakis (triphenylphosphine) palladium (0.387 g, 0.335 mmol) were combined in a 50 mL Schlenk flask. After the system was placed under vacuum and backfilled with argon three times, 50 mL of anhydrous toluene was injected. The reaction was heated at 105° C. for 3 days and then cooled to room temperature. The toluene solvent was removed by a rotary evaporator, and the resulting residue was purified on a silica gel column with hexane/dichloromethane (v/v, 1/1) as the eluent. Recrystallization from the mixture solvent of IPA/methanol produced a yellow crystal as product (1.4 g, 63.0%). FIG. 1 depicts the reaction of 4,7-Dibromo-5-chloro-2,1,3-benzothiadiazole and tributyl(thiophen-2-yl) stannane to produce 4-bromo-5-chloro-7-(thiophen-2-yl) benzo[c][1,2,5]thiadiazole. FIG. 2 depicts the NMR of 4-bromo-5-chloro-7-(thiophen-2-yl)benzo[c][1,2,5]thiadiazole.

Figure 3:
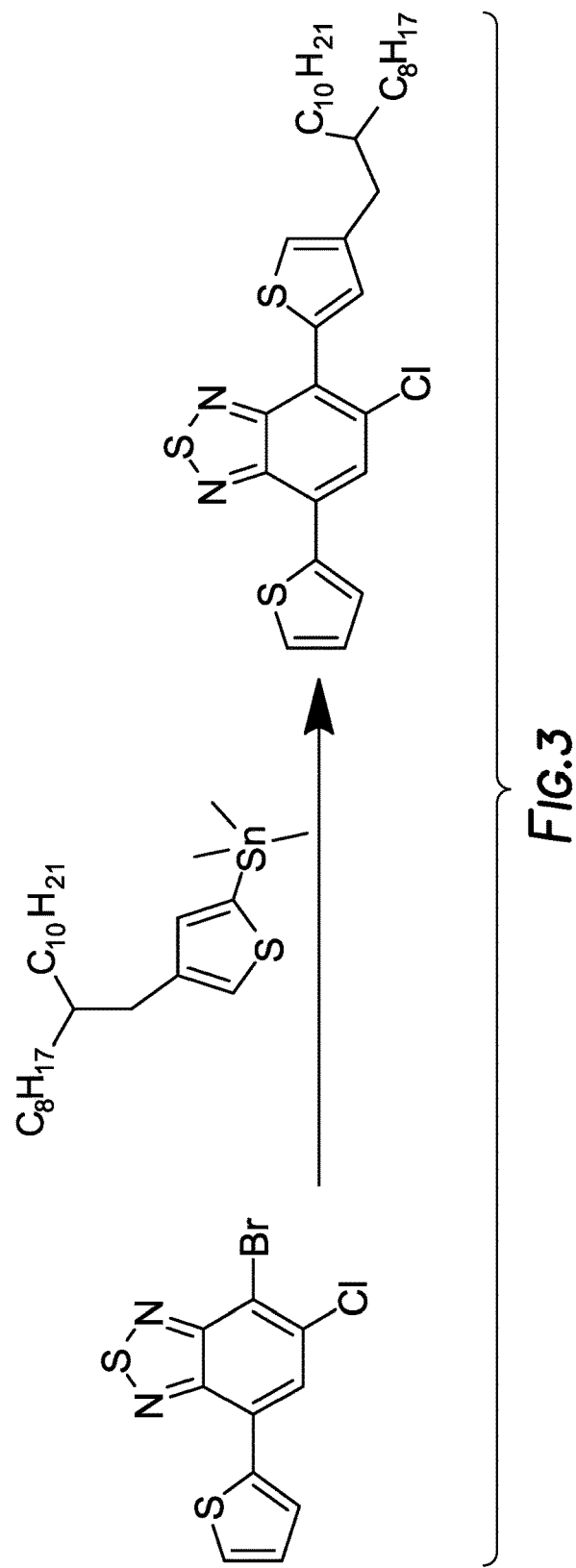
FIG. 3, depicts the reaction of trimethyl[4-(2-octyldodecyl)thiophen-2-yl]stannane and 4-bromo-5-chloro-7-(thiophen-2-yl)benzo[c][1,2,5]thiadiazole to produce 5-chloro-4-(4-(2-octyldodecyl)thiophen-2-yl)-7-(thiophen-2-yl)benzo[c][1,2,5]thiadiazole.
Figure 4:
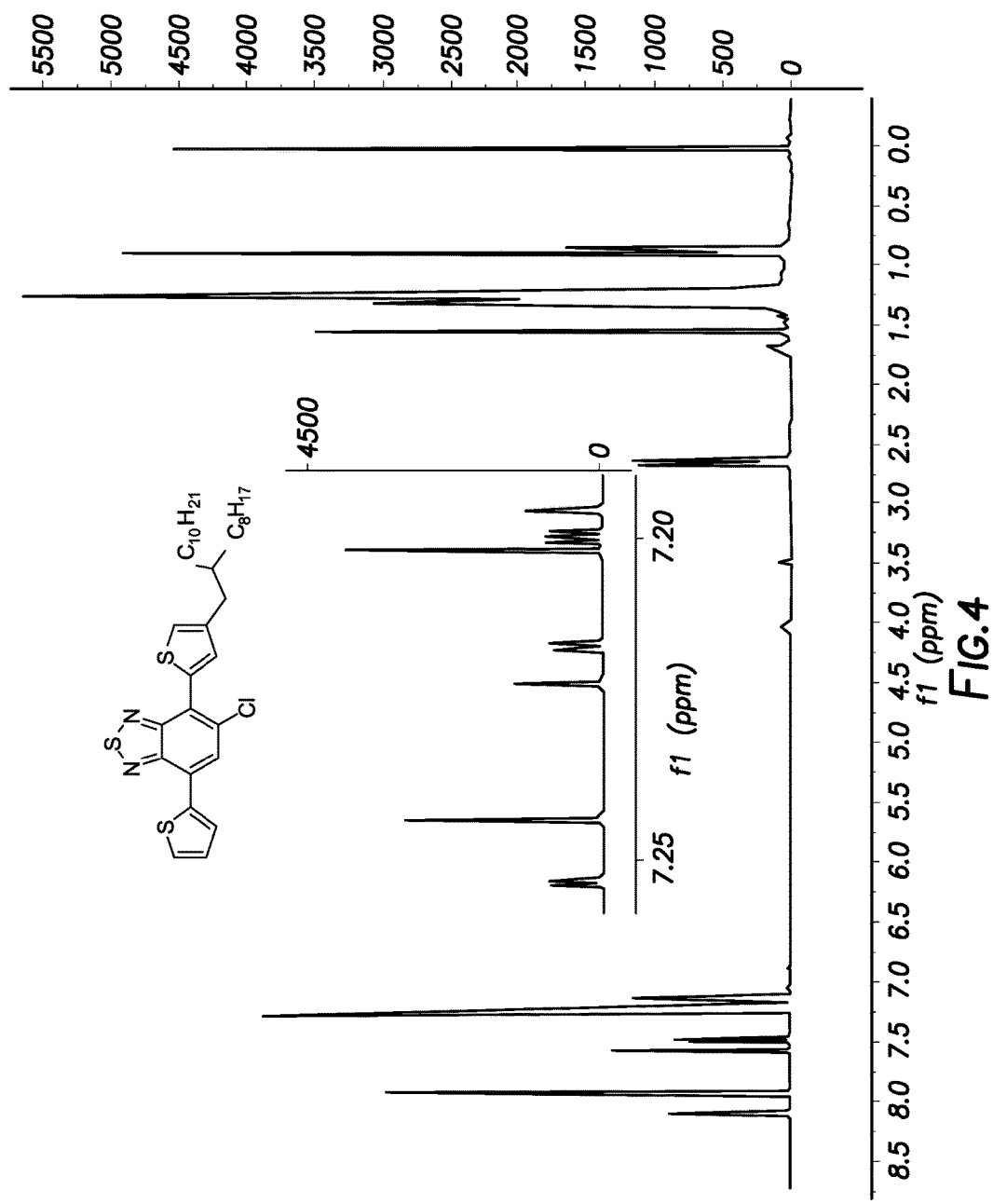
FIG. 4, depicts the NMR of 5-chloro-4-(4-(2-octyldodecyl)thiophen-2-yl)-7-(thiophen-2-yl)benzo[c][1,2,5]thiadiazole.

The next step involves the synthesis of 5-chloro-4-(4-(2-octyldodecyl)thiophen-2-yl)-7-(thiophen-2-yl)benzo[c][1,2,5]thiadiazole. Trimethyl[4-(2-octyldodecyl)thiophen-2-yl] stannane (2.449 g, 4.644 mmol), 4-bromo-5-chloro-7-(thiophen-2-yl)benzo[c][1,2,5]thiadiazole 6 (1.4 g, 4.221 mmol), $Pd_2dba_3$ (0.155 g, 0.169 mmol), and P(o-tol)$_3$ (0.206 g, 0.675 mmol) were combined in a 50 mL Schlenk flask. After the system was placed under vacuum and backfilled with argon three times, 15 mL of anhydrous toluene was injected. The reaction was heated at 105° C. for 2 days and cooled to room temperature. The toluene solvent was removed by a rotary evaporator, and the resulting residue was purified on a silica gel column with hexane/dichloromethane (v/v, 3/1) as the eluent. Recrystallization from the mixture solvent of IPA/methanol produced a red crystalline product (2.1 g, 80.8%). FIG. 3 depicts the reaction of trimethyl[4-(2-octyldodecyl)thiophen-2-yl]stannane and 4-bromo-5-chloro-7-(thiophen-2-yl)benzo[c][1,2,5]thiadiazole to produce 5-chloro-4-(4-(2-octyldodecyl)thiophen-2-yl)-7-(thiophen-2-yl)benzo[c][1,2,5]thiadiazole. FIG. 4 depicts the NMR of 5-chloro-4-(4-(2-octyldodecyl)thiophen-2-yl)-7-(thiophen-2-yl)benzo[c][1,2,5]thiadiazole.

Figure 5:
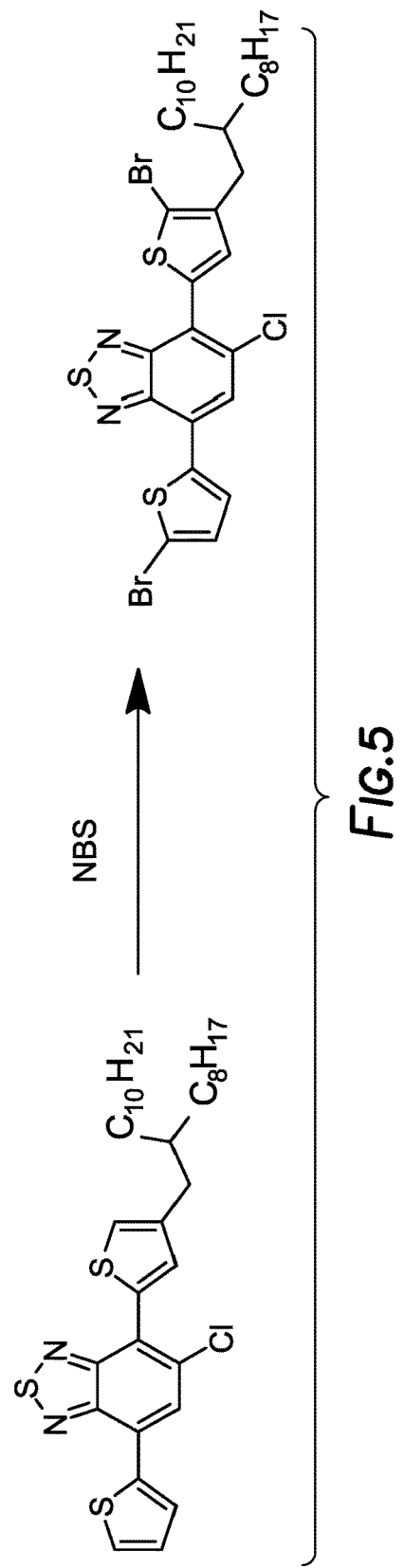
FIG. 5, depicts the reaction of 5-chloro-4-(4-(2-octyldodecyl)thiophen-2-yl)-7-(thiophen-2-yl)benzo[c][1,2,5]thiadiazole to 4-(5-bromo-4-(2-octyldodecyl)thiophen-2-yl)-7-(5-bromothiophen-2-yl)-5-chlorobenzo[c][1,2,5]thiadiazole.
Figure 6:
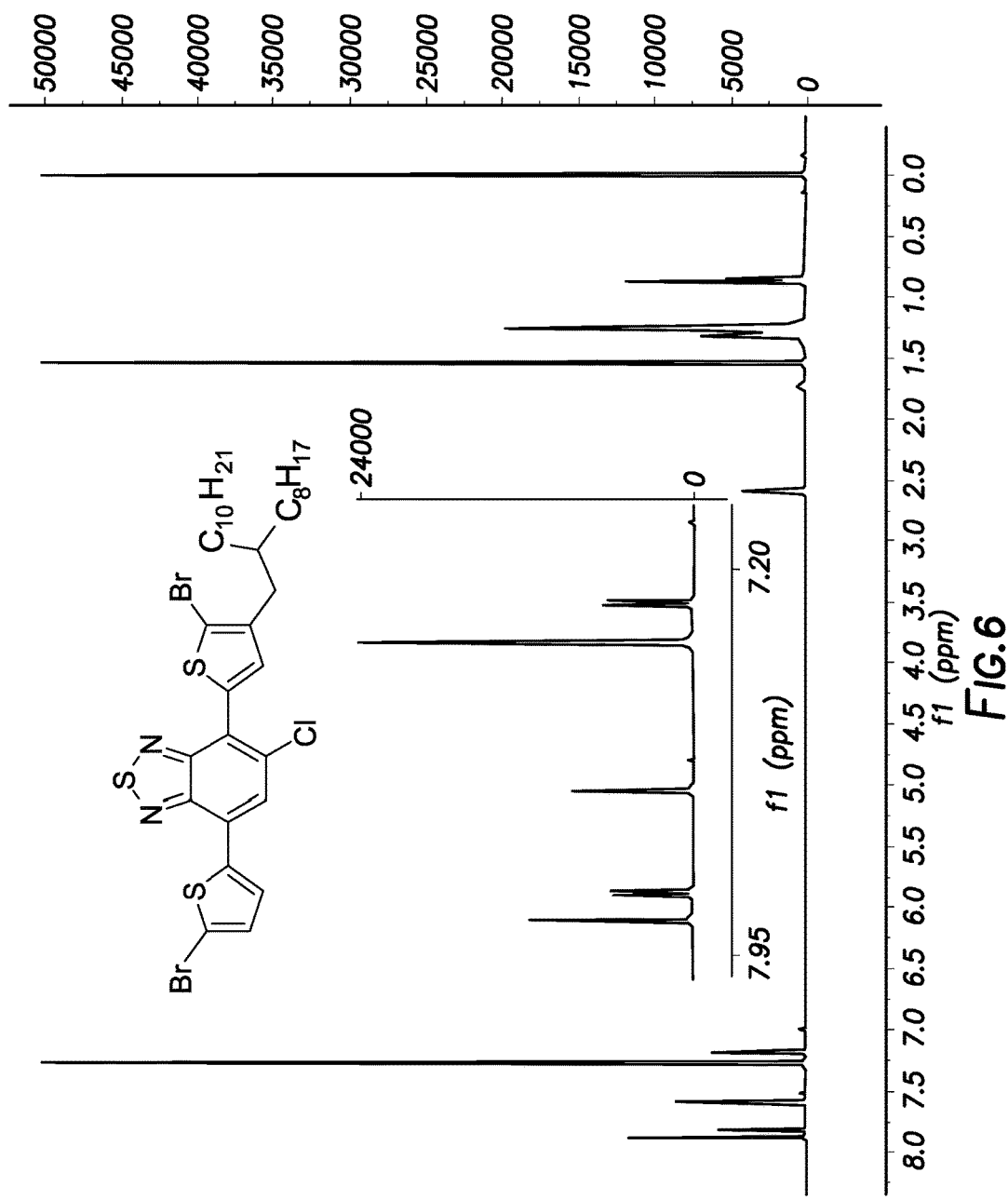
FIG. 6, depicts the NMR of 4-(5-bromo-4-(2-octyldodecyl)thiophen-2-yl)-7-(5-bromothiophen-2-yl)-5-chlorobenzo[c][1,2,5]thiadiazole.

The next step involves the synthesis of 4-(5-bromo-4-(2-octyldodecyl)thiophen-2-yl)-7-(5-bromothiophen-2-yl)-5-chlorobenzo[c][1,2,5]thiadiazole. 5-chloro-4-(4-(2-octyldodecyl)thiophen-2-yl)-7-(thiophen-2-yl)benzo[c][1,2,5] thiadiazole 7 (2.09 g, 3.396 mmol) was added to a 100 mL Schlenk flask followed by 50 mL of anhydrous THF. The solution was cooled to 0° C. before N-bromosuccinimide (1.269 g, 7.132 mmol) was added in portions. The reaction was stirred overnight. The reaction was stopped by adding saturated potassium carbonate solution and then extracted with hexane. The combined organic layer was dried over anhydrous $MgSO_4$. After the removal of solvent, the resulting mixture was subjected to column purification with hexane as the eluent. Red crystal (1.91 g, 72.7%) was obtained as product after recrystallization in isopropanol and drying under vacuum. FIG. 5 depicts the reaction of 5-chloro-4-(4-(2-octyldodecyl)thiophen-2-yl)-7-(thiophen-2-yl)benzo[c][1,2,5]thiadiazole to 4-(5-bromo-4-(2-octyldodecyl)thiophen-2-yl)-7-(5-bromothiophen-2-yl)-5-chlorobenzo[c][1,2,5]thiadiazole. FIG. 6 depicts the NMR of 4-(5-bromo-4-(2-octyldodecyl)thiophen-2-yl)-7-(5-bromothiophen-2-yl)-5-chlorobenzo[c][1,2,5]thiadiazole.

Figure 7:
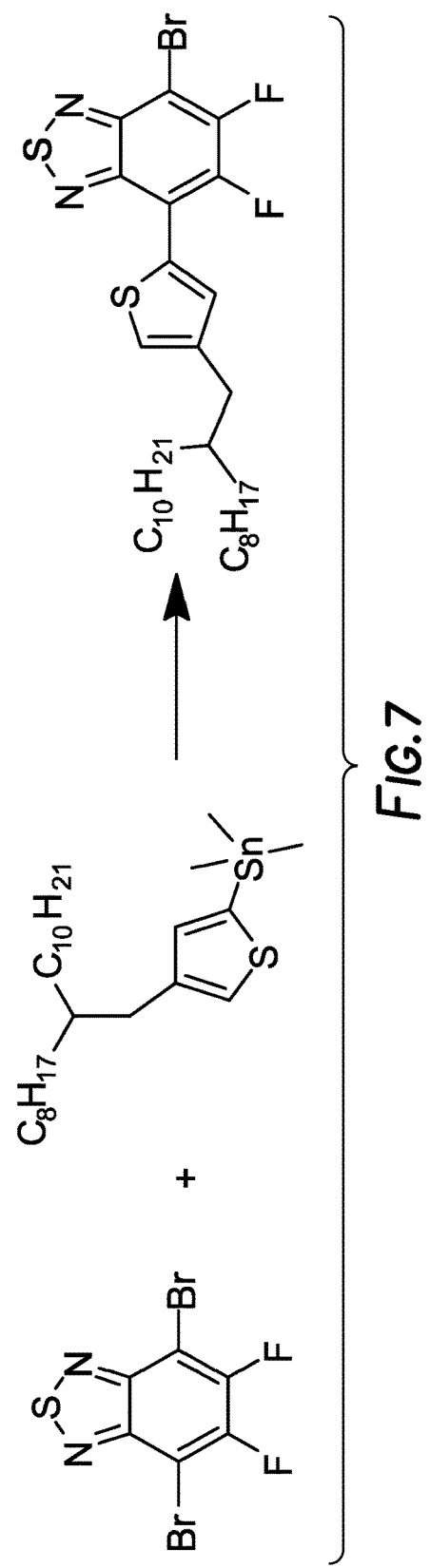
FIG. 7, depicts the synthesis of 4-bromo-5,6-difluoro-7-[4-(2-octyldodecyl)thiophen-2-yl]-2,1,3-benzothiadiazole.
Figure 8:
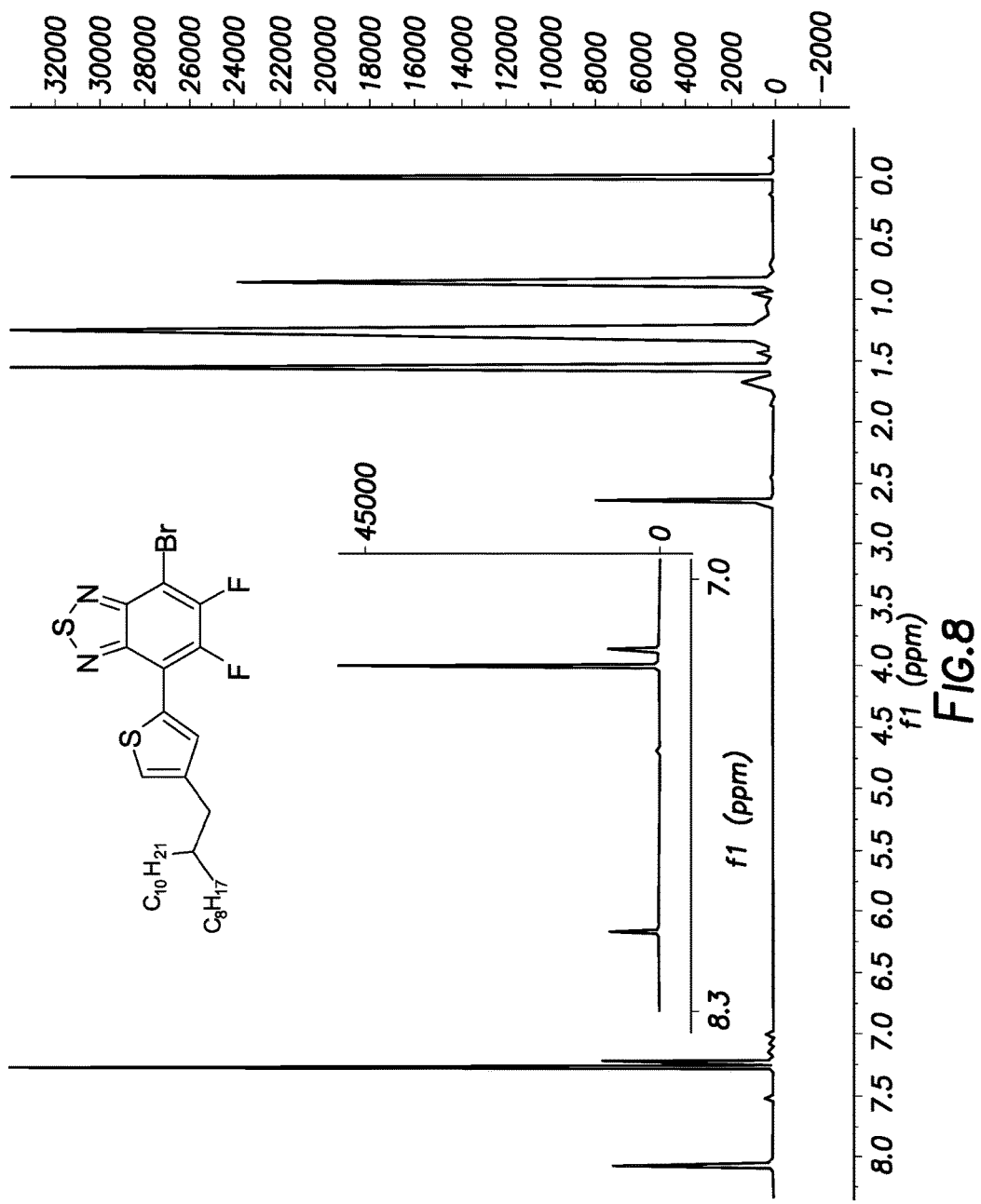
FIG. 8, depicts the NMR of 4-bromo-5,6-difluoro-7-[4-(2-octyldodecyl)thiophen-2-yl]-2,1,3-benzothiadiazole.

Synthesis of 4-bromo-5,6-difluoro-7-[4-(2-octyldodecyl) thiophen-2-yl]-2,1,3-benzothiadiazole is depicted in FIG. 7: Trimethyl[4-(2-octyldodecyl)thiophen-2-yl]stannane (1.759 g, 3.334 mmol), 4,7-dibromo-5,6-difluoro-2,1,3-benzothiadiazole (1 g, 3.031 mmol) and tetrakis(triphenylphosphine) palladium (0.175 g, 0.152 mmol) were combined in a 100 mL Schlenk flask. After the system was placed under vacuum and backfilled with argon three times, 30 mL of anhydrous toluene was injected. The reaction was heated at 105° C. for 48 h and cooled to room temperature. The toluene solvent was removed by a rotary evaporator, and the resulting residue was purified by using a silica gel column with hexane/chloroform mixture (v/v, 95/5) as the eluent. Removal of the solvent finally produced a yellow crystal as product (0.2 g, 10.8%). The NMR spectrum is shown in FIG. 8.

Figure 9:
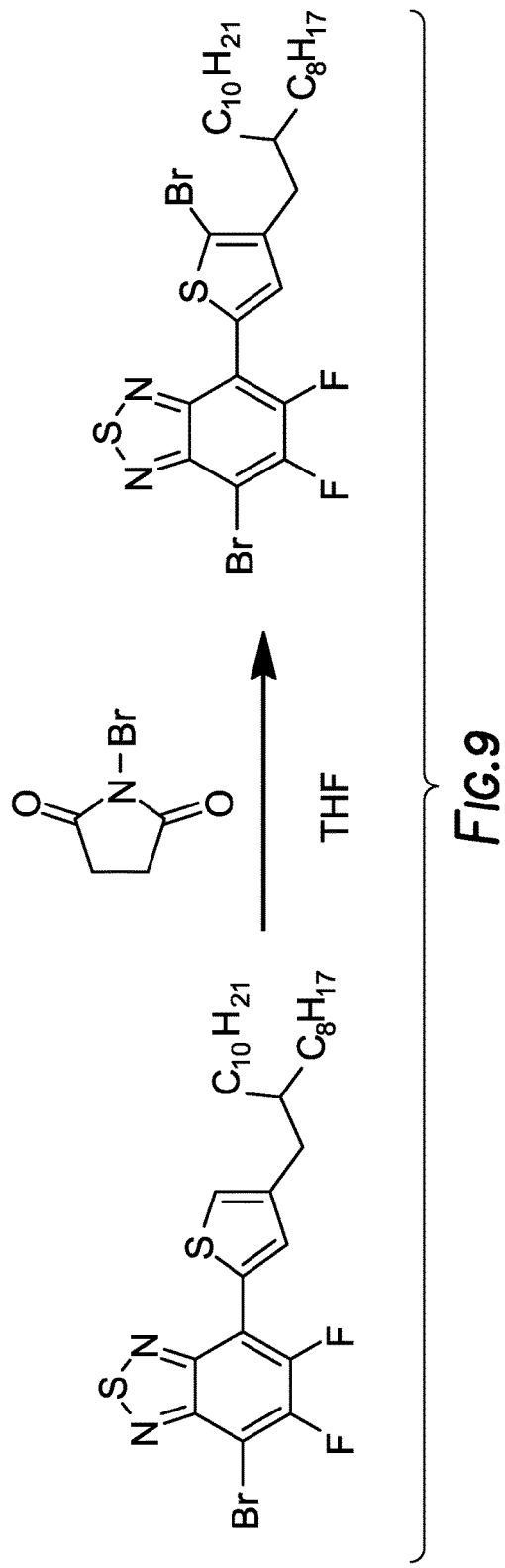
FIG. 9, depicts the synthesis of 4-bromo-7-(5-bromo-4-(2-octyldodecyl)thiophen-2-yl)-5,6-difluorobenzo[c][1,2,5]thiadiazole.

Synthesis of 4-bromo-7-(5-bromo-4-(2-octyldodecyl) thiophen-2-yl)-5,6-difluorobenzo[c][1,2,5]thiadiazole is depicted in FIG. 9: 4-bromo-5,6-difluoro-7-[4-(2-octyldodecyl)thiophen-2-yl]-2,1,3-benzothiadiazole (2.14 g, 3.487 mmol) was added to a 100 mL Schlenk flask followed by 60 mL of anhydrous tetrahydrofuran (THF). The solution was cooled to −78° C. before N-bromosuccinimide (0.652 g, 3.661 mmol) was added in portions with the absence of light. The reaction was stirred overnight. The reaction was stopped by adding saturated potassium carbonate solution and then was extracted with hexane. The combined organic layer was dried over anhydrous $MgSO_4$. After removal of the solvent, the resulting mixture was subjected to column purification with hexane as the eluent. A yellow crystal (0.83 g, 34.3%) was obtained as product after recrystallization in iso-propanol at −20° C. and being dried under vacuum at room temperature.

Figure 10:
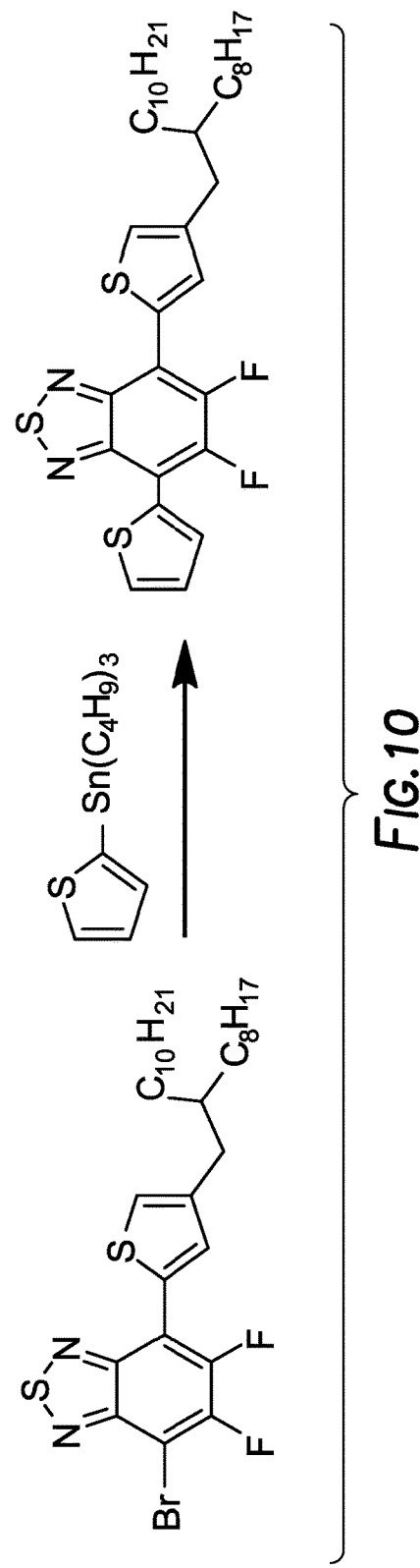
FIG. 10, depicts the synthesis of 5,6-difluoro-4-(4-(2-octyldodecyl)thiophen-2-yl)-7-(thiophen-2-yl)benzo[c][1,2,5]thiadiazole.
Figure 11:
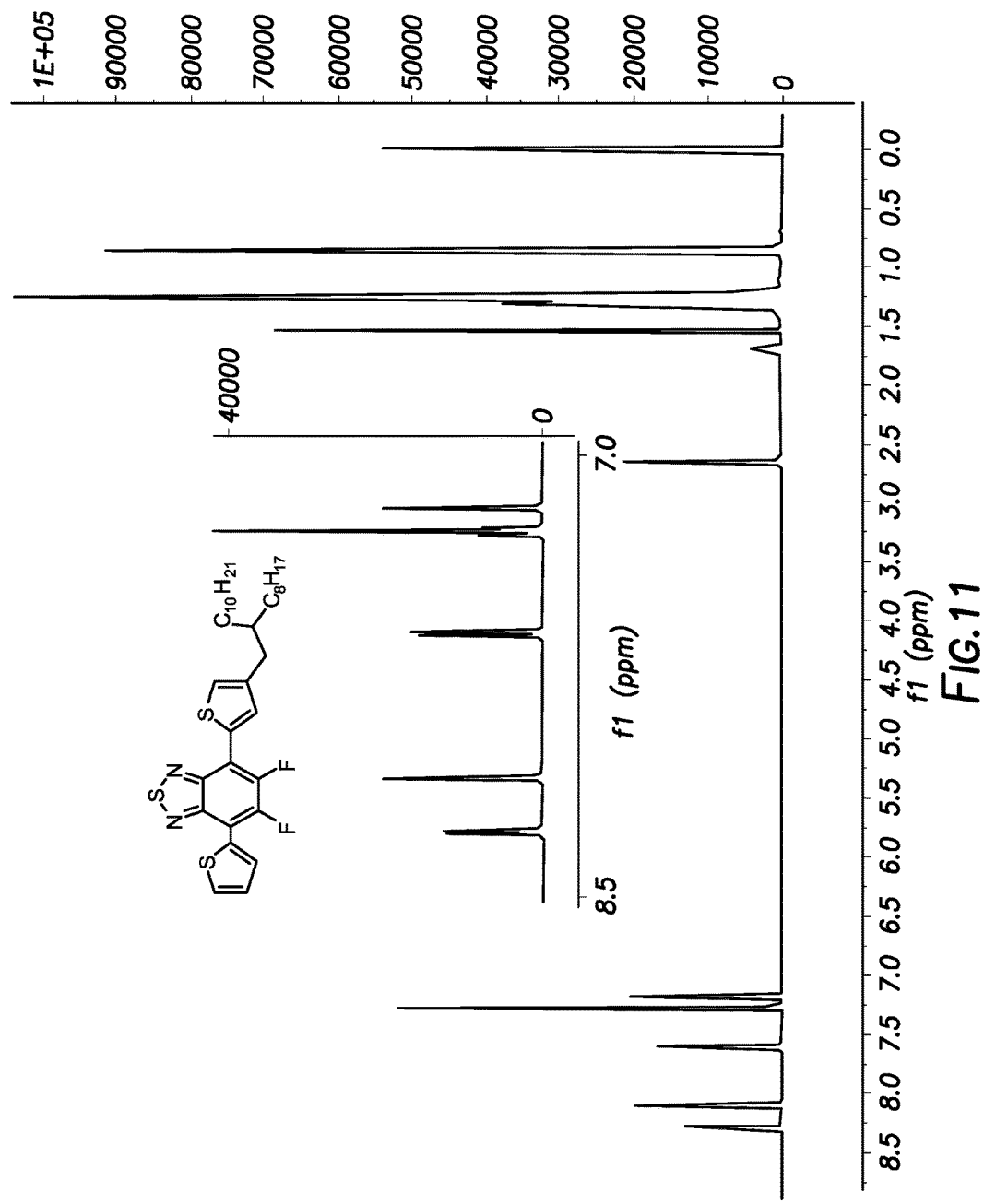
FIG. 11, depicts the NMR of 5,6-difluoro-4-(4-(2-octyldodecyl)thiophen-2-yl)-7-(thiophen-2-yl)benzo[c][1,2,5]thiadiazole.

Synthesis of 5,6-difluoro-4-(4-(2-octyldodecyl)thiophen-2-yl)-7-(thiophen-2-yl)benzo[c][1,2,5]thiadiazole is depicted in FIG. 10: 4-bromo-5,6-difluoro-7-[4-(2-octyldodecyl)thiophen-2-yl]-2,1,3-benzothiadiazole (1.916 g, 0.003 mol), tributyl(thiophen-2-yl)stannane (1.282 g, 0.003 mol), and $Pd_2(dba)_3$ (57.177 mg, 0.062 mmol) and $P(o\text{-tol})_3$ (76.018 mg, 0.25 mmol) were combined in a 100 mL Schlenk flask. After the system was placed under vacuum and backfilled with argon three times, 20 mL of anhydrous toluene was injected. The reaction was heated at 105° C. for 2 days and cooled to room temperature. The toluene solvent was removed by a rotary evaporator, and the resulting residue was purified by using a silica gel column with hexane/dichloromethane mixture (v/v, 92/8) as the eluent. Recrystallization from the mixture solvent of iso-propanol (IPA)/hexane finally produced a yellow crystal as product (1.65 g, 85.9%). The NMR of 6-difluoro-4-(4-(2-octyldodecyl)thiophen-2-yl)-7-(thiophen-2-yl)benzo[c][1,2,5]thiadiazole is depicted in FIG. 11.

Figure 12:
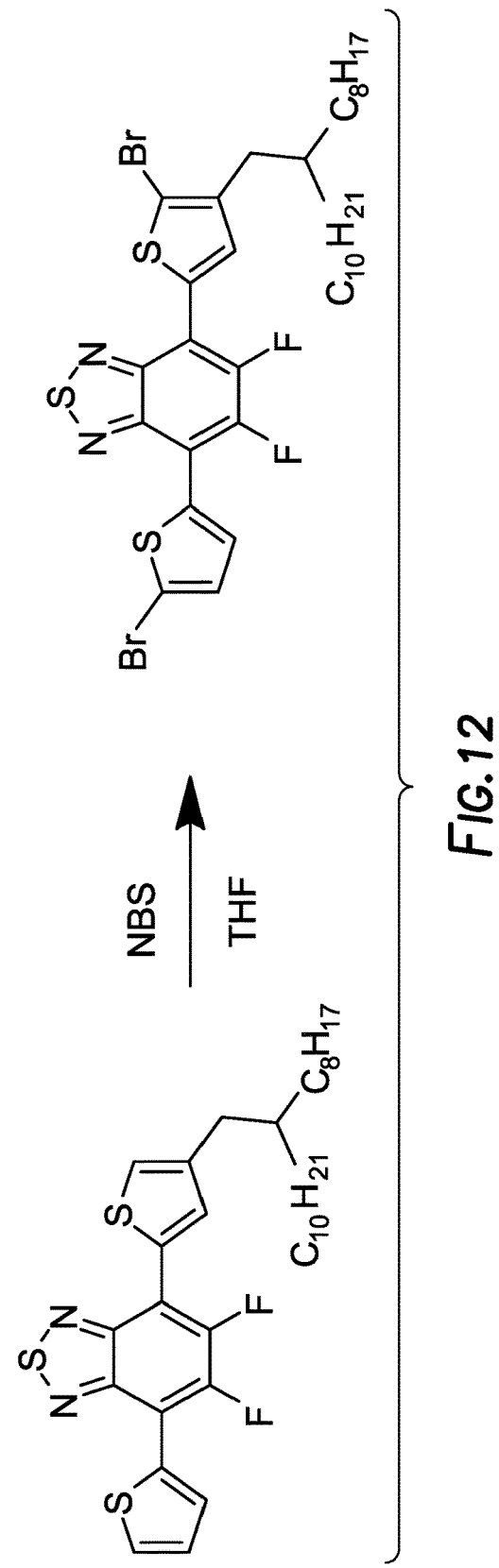
FIG. 12, depicts the synthesis of 4-(5-bromo-4-(2-octyldodecyl)thiophen-2-yl)-7-(5-bromothiophen-2-yl)-5,6-difluorobenzo[c][1,2,5]thiadiazole.
Figure 13:
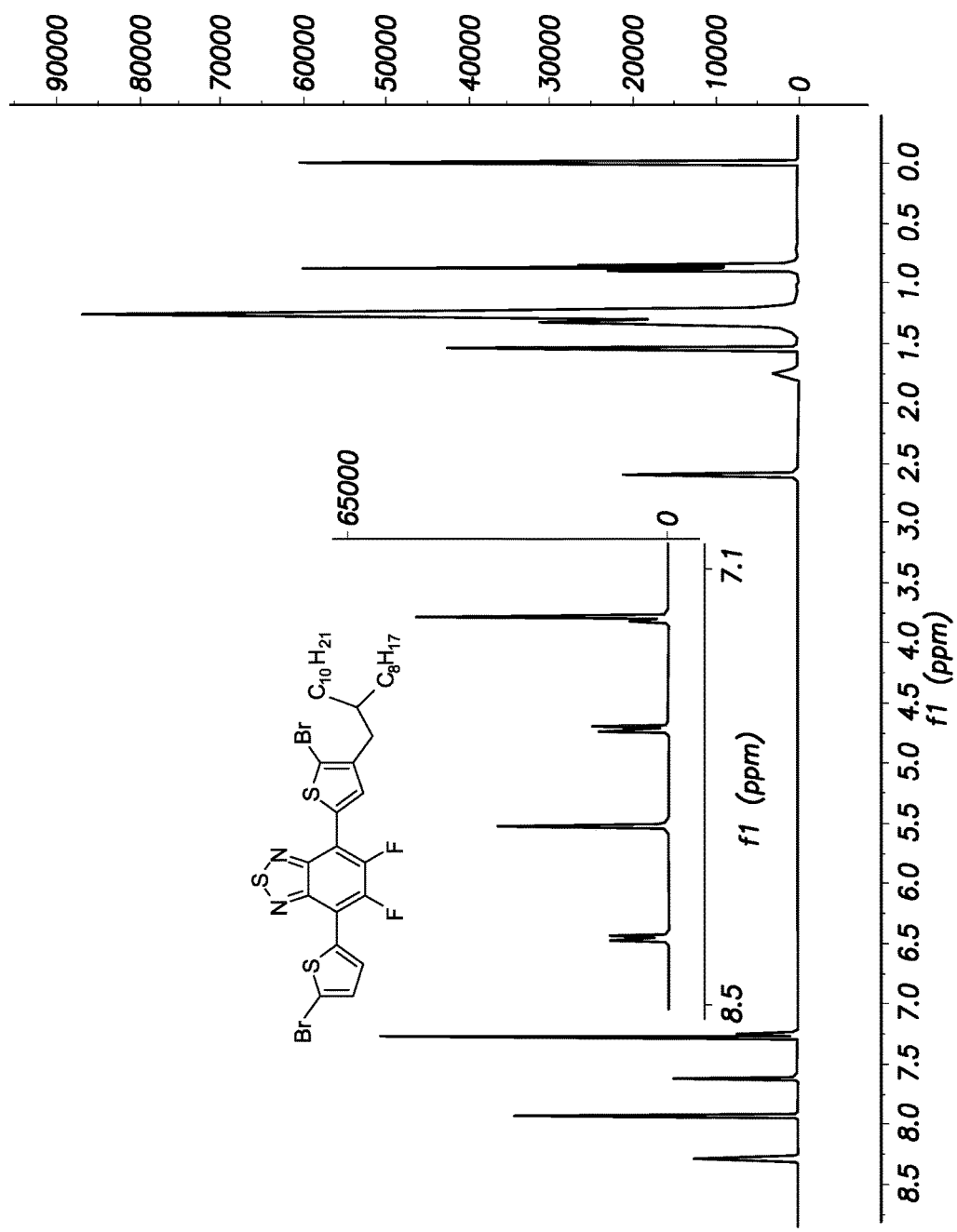
FIG. 13, depicts the NMR of 4-(5-bromo-4-(2-octyldodecyl)thiophen-2-yl)-7-(5-bromothiophen-2-yl)-5,6-difluorobenzo[c][1,2,5]thiadiazole.

Synthesis of 4-(5-bromo-4-(2-octyldodecyl)thiophen-2-yl)-7-(5-bromothiophen-2-yl)-5,6-difluorobenzo[c][1,2,5]thiadiazole, is depicted in FIG. 12: 5,6-difluoro-4-(4-(2-octyldodecyl)thiophen-2-yl)-7-(thiophen-2-yl)benzo[c][1,2,5]thiadiazole (1.62 g, 2.626 mmol) was added to a 100 mL Schlenk flask followed by 50 mL of anhydrous tetrahydrofuran (THF). The solution was cooled to −78° C. before N-bromosuccinimide (0.486 g, 2.731 mmol) was added in portions in dark. The reaction was stirred overnight. The reaction was stopped by adding saturated potassium carbonate solution and then was extracted with hexane. The combined organic layer was dried over anhydrous $MgSO_4$. After removal of the solvent, the resulting mixture was subjected to column purification with hexane as the eluent. A orange wax solid (1.36 g, 66.9%) was obtained as product after recrystallization in iso-propanol and being dried in vacuo at room temperature. The NMR is depicted in FIG. 13.

The following examples of certain embodiments of the invention are given. Each example is provided by way of explanation of the invention, one of many embodiments of the invention, and the following examples should not be read to limit, or define, the scope of the invention.

Example 1

Figure 14:
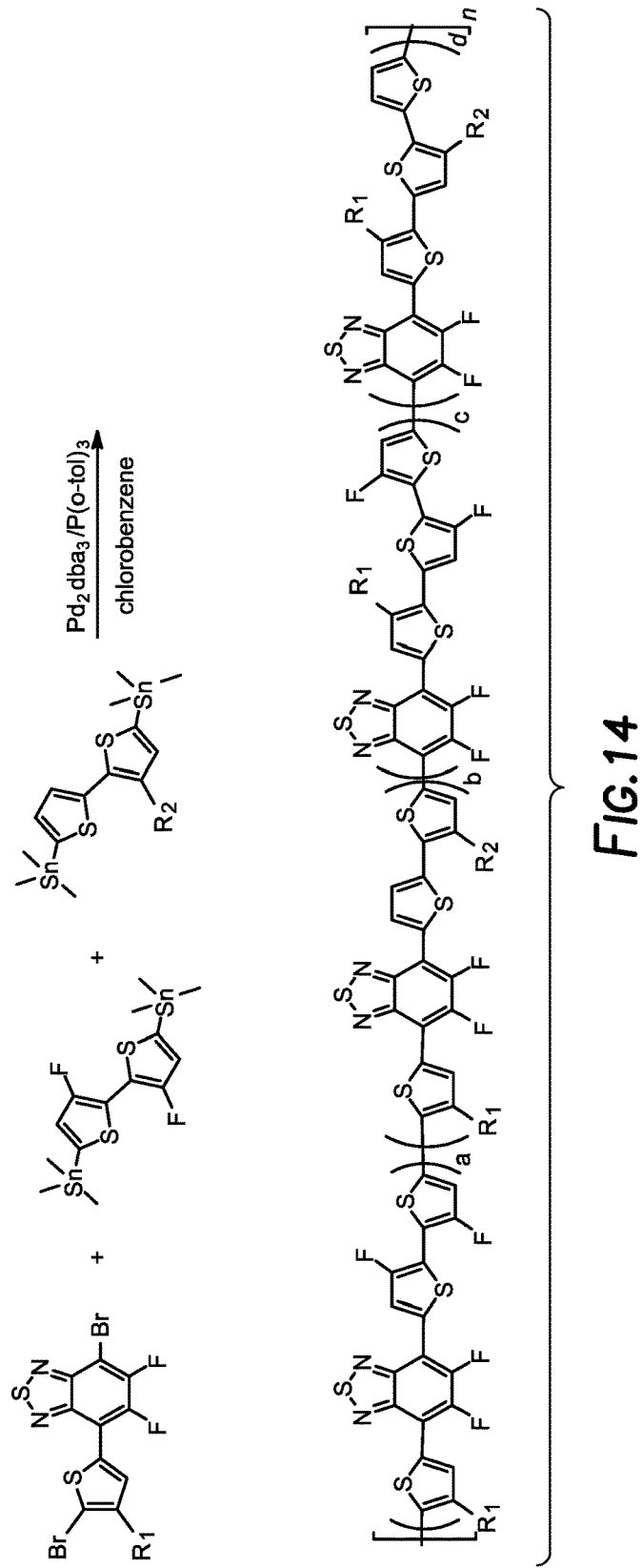
FIG. 14, depicts the reaction of Example 1.

In a 25 mL Schlenk flask, 4-bromo-7-[5-bromo-4-(2-octyldodecyl)thiophen-2-yl]-5,6-difluoro-2,1,3-benzothiadiazole (147.3 mg, 0.213 mmol), (3,3'-difluoro-[2,2'-bithiophene]-5,5'-diyl)bis(trimethylstannane) (35.088 mg, 0.066 mmol), [4-(2-hexyldecyl)-5-[5-(trimethylstannyl)thiophen-2-yl]thiophen-2-yl]trimethylstannane (111.1 mg, 0.155 mmol) and $Pd_2dba_3$ (4.058 mg, 0.004 mmol) and $P(o\text{-tol})_3$ (5.395 mg, 0.018 mmol) were combined. The mixture was placed under vacuum and backfilled with argon twice before 2.3 mL of anhydrous chlorobenzene was added. The solution was heated to 130° C. for 66 h. The reaction was stopped by being cooled to room temperature. The product was precipitated by adding into methanol and was further purified by Soxhlet extraction, using acetone (6 h), hexane (24 h), dichloromethane (24 h) and chloroform (16 h) as the solvents. The portion obtained from chloroform was the main product (169 mg, yield 90.2%) after precipitation from methanol and then drying overnight. FIG. 14 depicts the reaction of this coupling.

Example 2

Figure 15:
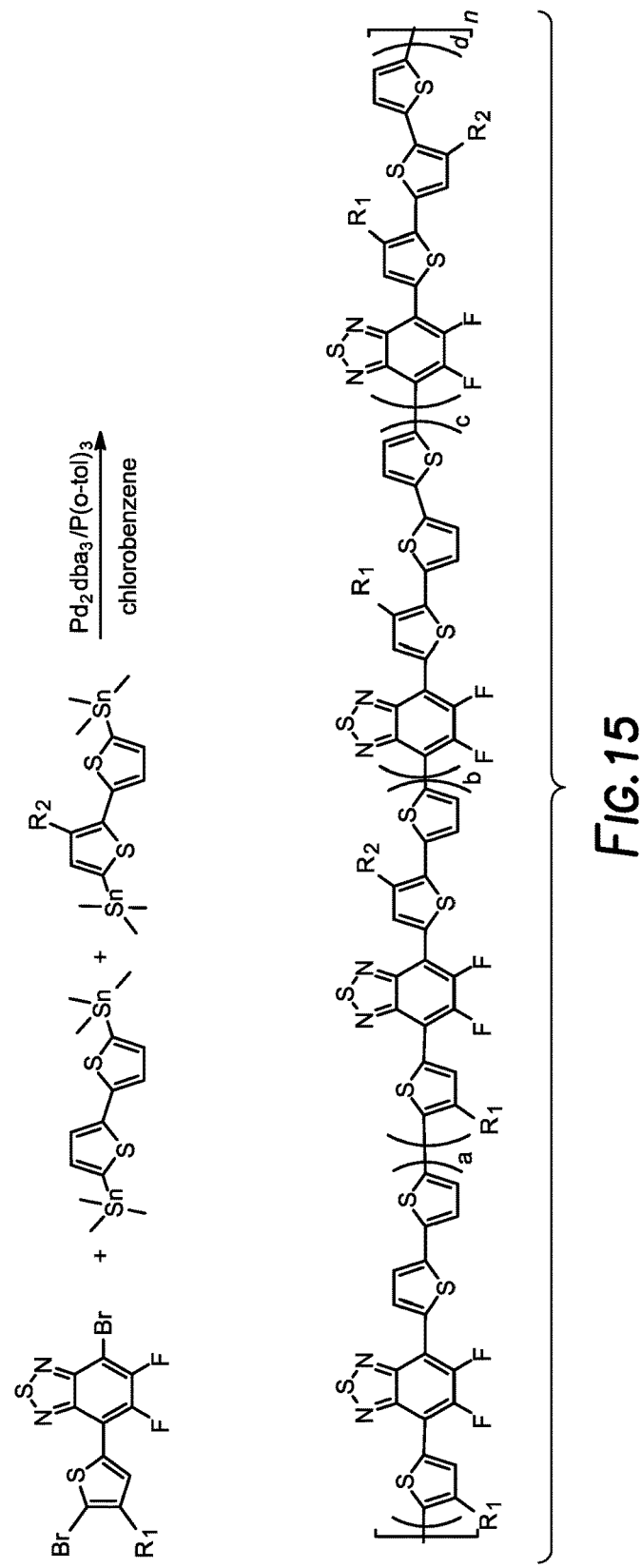
FIG. 15, depicts the reaction of Example 2.
Figure 16:
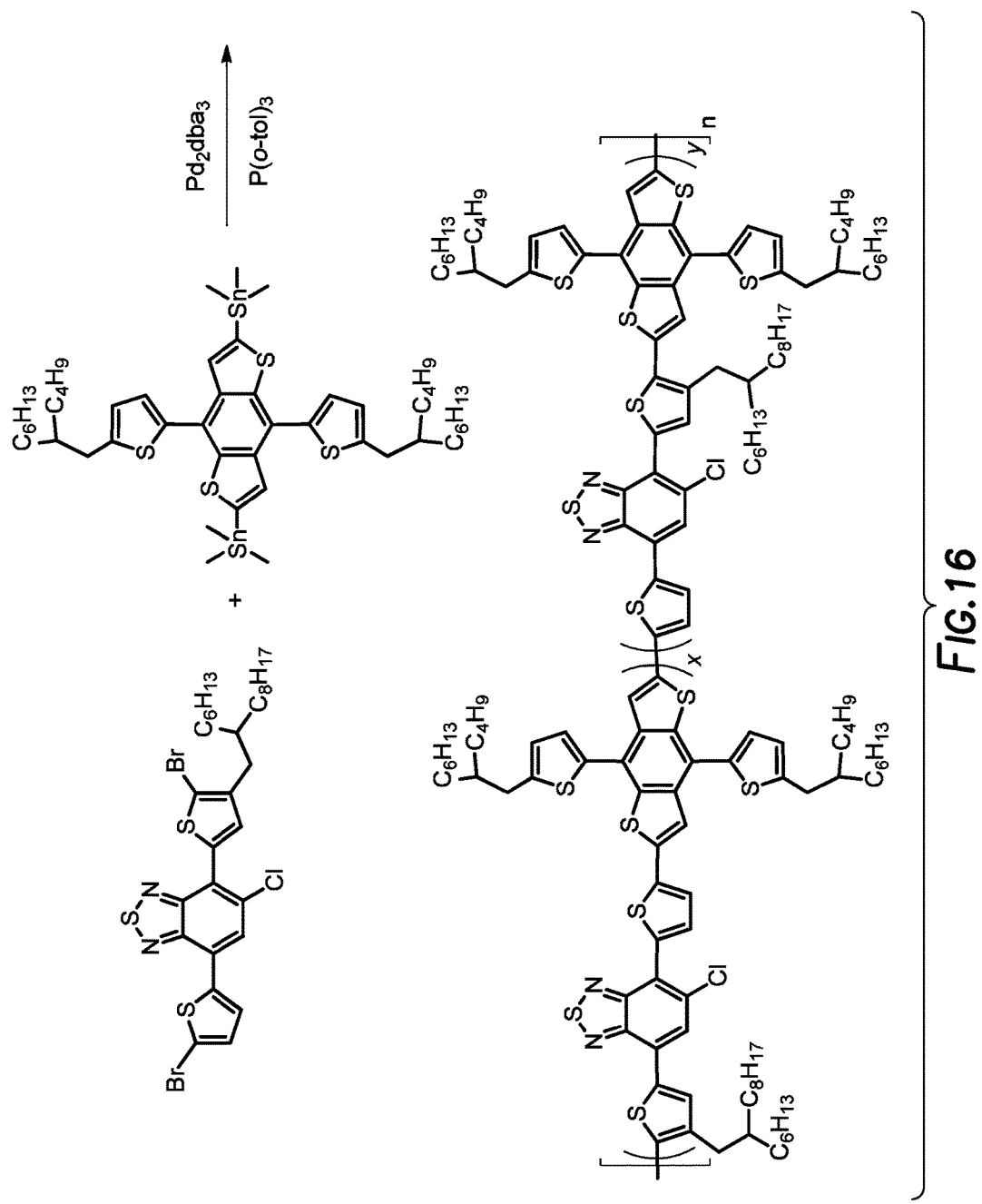
FIG. 16, depicts the reaction of Example 3.

In a 10 mL Schlenk flask, 4-bromo-7-[5-bromo-4-(2-octyldodecyl)thiophen-2-yl]-5,6-difluoro-2,1,3-benzothiadiazole (125.498 mg, 0.181 mmol), trimethyl({5-[5-(trimethylstannyl)thiophen-2-yl]thiophen-2-yl})stannane (46.42 mg, 0.094 mmol), [4-(2-hexyldecyl)-5-[5-(trimethylstannyl)thiophen-2-yl]thiophen-2-yl]trimethylstannane (67.6 mg, 0.094 mmol) and $Pd_2dba_3$ (3.457 mg, 0.004 mmol) and $P(o\text{-tol})_3$ (4.596 mg, 0.015 mmol) were combined. The mixture was placed under vacuum and backfilled with argon twice before 1.9 mL of anhydrous chlorobenzene was added. The solution was heated to 130° C. for 66 h. The reaction was stopped by being cooled to room temperature. The product was precipitated by adding into methanol and was further purified by Soxhlet extraction, using acetone (4 h), hexane (16 h), dichloromethane (4 h), chloroform (4 h) and chlorobenzene (5 h) as the solvents. The portion obtained from chlorobenzene was the main product (120 mg, yield 81.9%) after precipitation from methanol and then drying overnight. FIG. 15 depicts the reaction of this coupling.

Example 3

In a 25 mL of Schlenk flask, (4,8-bis(5-(2-butyloctyl)thiophen-2-yl)benzo[1,2-b:4,5-b']dithiophene-2,6-diyl)bis(trimethylstannane) (120.7 mg, 118.707 μmol), 4-[5-bromo-4-(2-hexyldecyl)thiophen-2-yl]-7-(5-bromothiophen-2-yl)-5-chloro-2,1,3-benzothiadiazole (81.07 mg, 0.113 mmol), $Pd_2dba_3$ (2.071 mg, 0.002 mmol), and $P(o\text{-tol})_3$ (5.506 mg, 0.018 mmol) were combined. The mixture was placed under vacuum and backfilled with argon twice before 2.3 mL of anhydrous chlorobenzene was added. The solution was heated at 135° C. for 18 hours, and then the mixture was precipitated from methanol after being cooled to room temperature. The product was precipitated out in 40 mL methanol and purified by Soxhlet extraction, using acetone (4 hours), hexane (16 hours), and dichloromethane (4 hours) as solvents. The dichloromethane portion was the main product (99.4 mg, 67.1%) after precipitation from methanol and then drying overnight.

Example 4

Figure 17:
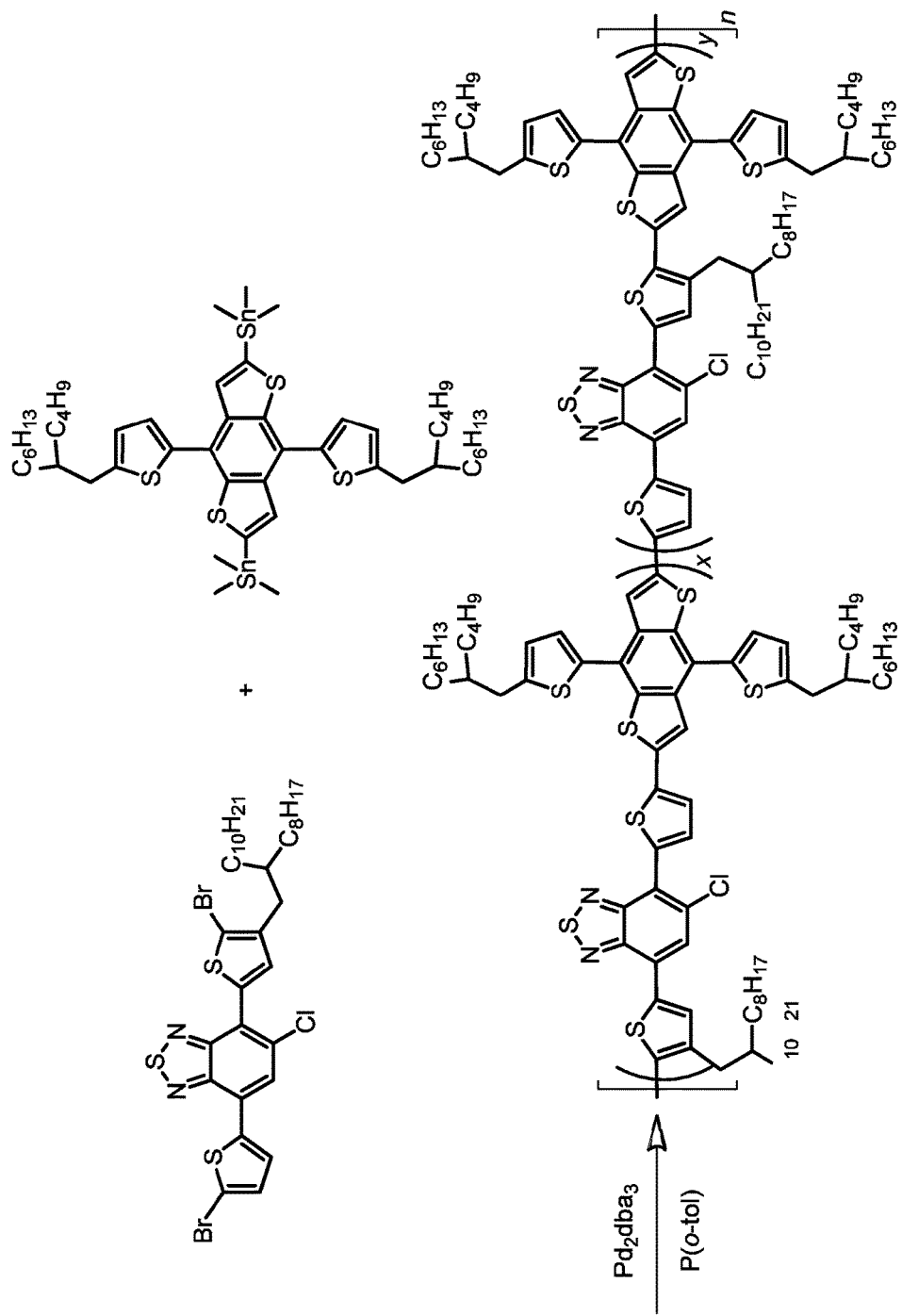
FIG. 17, depicts the reaction of Example 4.
Figure 18:
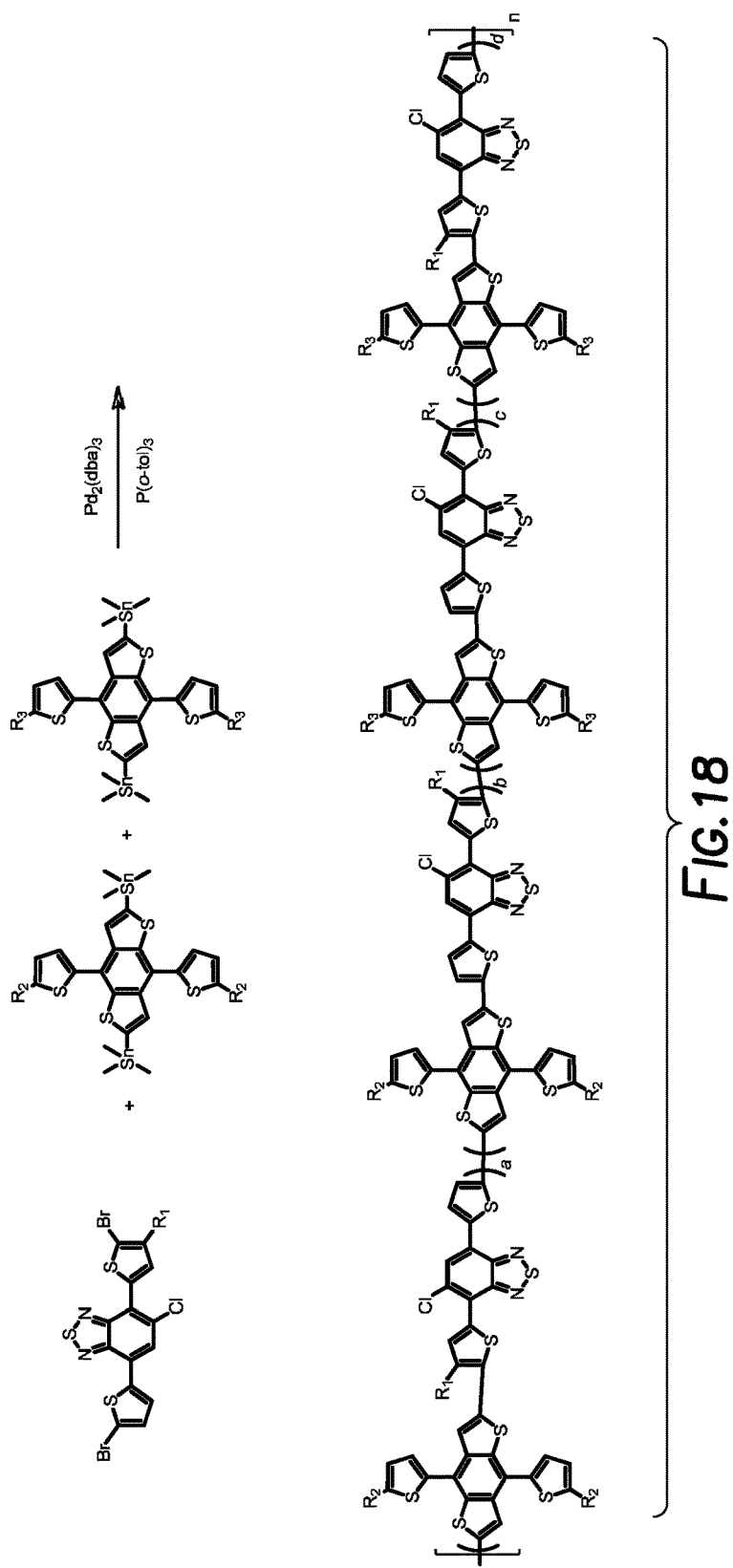
FIG. 18, depicts the reaction of Example 5

In a 25 mL Schlenk flask, 4-(5-bromo-4-(2-octyldodecyl)thiophen-2-yl)-7-(5-bromothiophen-2-yl)-5-chlorobenzo[c][1,2,5]thiadiazole 4 (72.4 mg, 0.094 mmol), (4,8-bis(5-(2-butyloctyl)thiophen-2-yl)benzo[1,2-b']dithiophene-2,6-diyl)bis(trimethylstannane) (100.0 mg, 0.098 mmol), Pd2dba3 (3.4 mg, 0.004 mmol), and P(o-tol)3 (4.6 mg, 0.015 mmol) were combined. The mixture was placed under vacuum and backfilled with argon twice before 1.6 mL of anhydrous chlorobenzene was added. The solution was heated at 130° C. for 18 hours, and then 20 mL of chloroform was added and the mixture was precipitated from methanol. The product was precipitated out in 40 mL methanol and purified by Soxhlet extraction, using methanol (4 hours), hexane (16 hours), and chloroform (3 hours) as solvents. The chloroform portion was the main product (113 mg, 88.1%) after precipitation from methanol and then drying overnight. The viscosity in chlorobenzene (10 mg/mL) was 1.105 mPa·s at 25.3° C. FIG. 17 depicts the reaction mechanism of this coupling.

Example 5

In a 25 mL of Schlenk flask, (4,8-bis(5-(2-ethylhexyl) thiophen-2-yl)benzo[1,2-b:4,5-b']dithiophene-2,6-diyl)bis (trimethylstannane) (34.482 mg, 0.038 mmol), (4,8-bis(5-(2-butyloctyl)thiophen-2-yl)benzo[1,2-b:4,5-b'] dithiophene-2,6-diyl)bis(trimethylstannane) (58.139 mg, 0.057 mmol), 4,7-bis[5-bromo-4-(2-octyldodecyl)thiophen-2-yl]-5,6-difluoro-2,1,3-benzothiadiazole 7 (106 mg, 0.1 mmol), Pd2dba3 (3.68 mg, 0.004 mmol), and P(o-tol)3 (4.9 mg, 0.016 mmol) were combined. The mixture was placed under vacuum and backfilled with argon twice before 5.0 mL of anhydrous chlorobenzene was added. The solution was heated at 130° C. for 18 hours, and then the mixture was precipitated from methanol after being cooled to room temperature. The product was precipitated out in 40 mL methanol and purified by Soxhlet extraction, using acetone (4 hours), hexane (16 hours), and chloroform (2 hours) as solvents. The chloroform portion was the main product (87 mg, 73.0%) after precipitation from methanol and then drying overnight. The viscosity in chlorobenzene/dichlorobenzene (v/v, 1/1) (10 mg/mL) was 2.058 mPa·s at 25.0° C.

Photovoltaic devices for Examples 1-6 were created using the methodology of device fabrication below.

Device Fabrication

Zinc tin oxide (ZTO):phenyl-$C_{60}$-butyric-N-(2-hydroxyethyl)acetamide (PCBNOH) sol-gel solutions were prepared by adding PCBNOH (1.7 mg, $2.4 \times 10^{-3}$ mmol), zinc acetate dihydrate (330 mg, 1.5 mmol), and tin (II) acetate (33 mg, 0.14 mmol) to 2-methoxyethanol (10.6 mL) and ethanolamine (92 μL, 1.5 mmol). Solutions were stirred in air for a minimum of 8 h before use. ITO-coated glass substrates were washed with detergent (2×15 min), DI water (2×15 min), acetone (2×15 min), and isopropanol (2×15 min) in an ultrasonication bath. The substrates were placed in an oven at 80° C. for 2+ hours and placed in a UV-ozone cleaner for 1 min. After filtration with a 0.2 μm PVDF syringe filter, ZTO:PCBNOH sol-gel was spin-coated onto the top of the ITO substrate at 4000 rpm for 40 s. The substrate was annealed at 210° C. in air for 15 min and taken into a glove box for deposition of the active layer. The photoactive layer solution was prepared by a 1:1.2 or 1:1.6 polymer:PCBM ratio at 14-27.5 mg/mL concentration with 1:1 ratio of chlorobenzene and 1,2-dichlorobenzene. See Table I for solution and casting conditions for each polymer. The solution was mixed in a glove box and heated at 80° C. for 12 hours. Afterward, 2.5 or 3 vol % of 1,8-diiodooctane was added. The photoactive layer solution and ZTO:PCBNOH coated ITO substrates were heated at 110° C. for 30 min. Spin coating was performed with the photoactive layer solution, and substrates were heated to 110° C. 80 μL was pipetted onto the hot substrate and spin coated at 600 rpm or 1000 rpm for 40 s, followed immediately by 1200 rpm for 2 s (only for P-27 and P-29). The substrates were placed in a closed glass Petri dish for 18 hours to allow for solvent annealing. After solvent annealing, the substrates were scratched at the edge to expose the ITO layer for cathode electrical connection. The substrates were then placed in the metal evaporator, and 3.5 nm of $MoO_x$ and 120 nm of Ag were deposited. The deposition rate for the $MoO_x$ was 1.5-2.3 Å/s and Ag was 1.7-2.5 Å/s. The devices were encapsulated by using UV-curable epoxy and a cover glass slide and exposed to a UV cure for 3 min.

Figure 19:
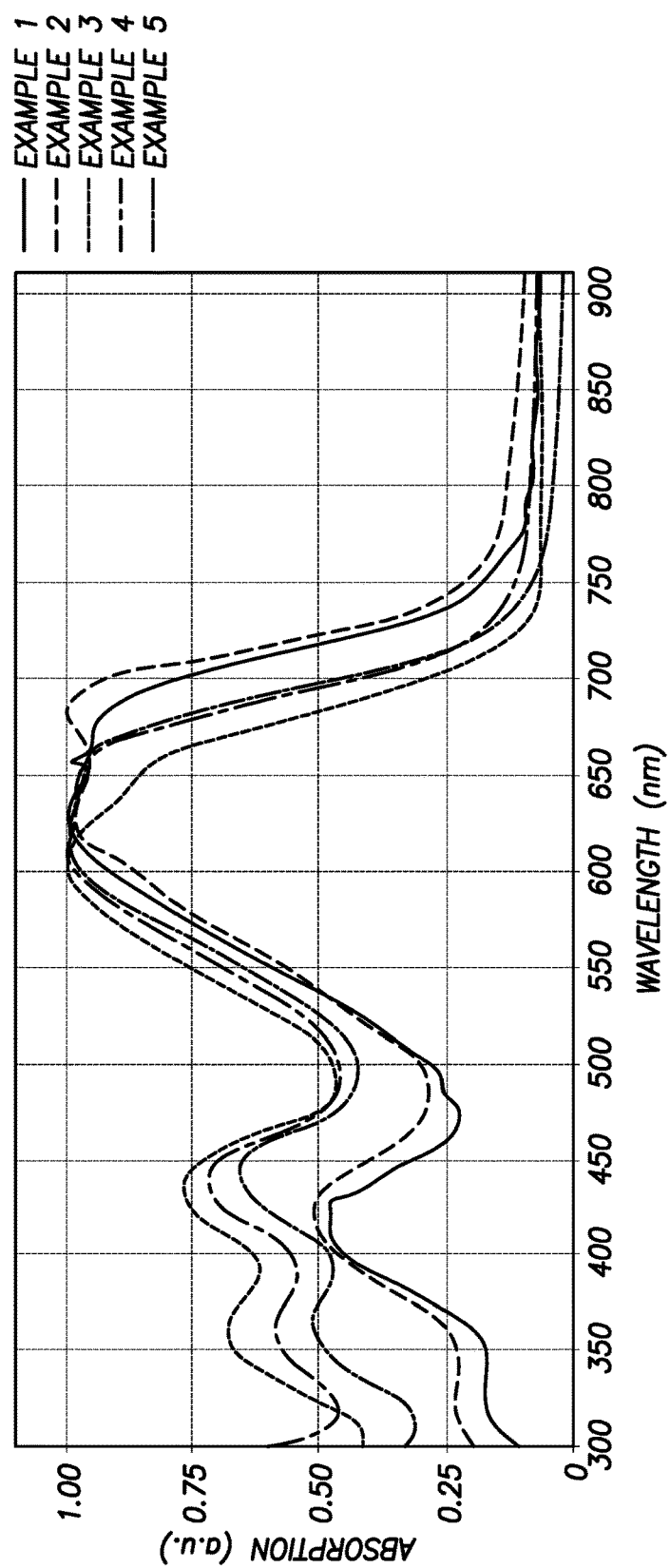
FIG. 19, depicts a comparison of the UV-vis spectra of Examples 1-5.

A comparison of the UV-vis spectra of Examples 1-5 with PCBM is shown in FIG. 19.

The device performances of Examples 1-5 in a polymer are listed below in Table 1.

TABLE 1

| Polymer Example | Voc (V) | Jsc (mA/cm$^2$) | Fill Factor % | Power Conversion Efficiency % | Rs (Ω cm$^2$) | Rsh (Ω cm$^2$) |
|---|---|---|---|---|---|---|
| 1 | 0.779 | 18.84 | 72.6 | 10.6 | 3.5 | 1390 |
| 2 | 0.718 | 19.5 | 72.3 | 10.1 | 3.1 | 2620 |
| 3 | 0.810 | 15.5 | 74.0 | 9.6 | 6.8 | 3000 |
| 4 | 0.829 | 17.3 | 74.3 | 10.4 | 3.1 | 2300 |
| 5 | 0.814 | 16.2 | 74.7 | 9.6 | 3.2 | 1900 |

Example 6

A 500 mL dry Schlenk flask was purged with argon before 3-dodecylthiophene (9.79 g, 0.039 mol) and N,N,N',N'-Tetramethylethylenediamine (TMEDA) (4.96 g, 0.043 mol) were added. Anhydrous THF (150 mL) was injected and the resulting solution was cooled to −78° C. n-Butyl lithium (2.5 M in hexane, 15.511 mL, 0.039 mol) was added dropwise by syringe. The reaction mixture was warmed to room temperature, and then heated to 60° C. for 1 hour. The reaction was again cooled to −78° C. and treated with a trimethyltin chloride solution (1.0 M in THF, 46.5 mL, 0.047 mol). The reaction was stirred overnight at room temperature. Water (100 mL) was poured into solution, the THF solvent was removed by rotary evaporator, and the aqueous layer was extracted with hexane (3×100 mL). The combined organic layers were washed with water (2×) and MeOH (1×) and then dried (Na2SO4), filtered, and concentrated to afford the product (12.8 g, 79.5%) as a colorless liquid.

(4-dodecylthiophen-2-yl)trimethylstannane (2.26 g, 5.4 mmol), 4-bromo-5-chloro-7-(thiophen-2-yl)benzo[c][1,2,5]thiadiazole (1.64 g, 4.95 mmol), Pd2(dba)3 (0.18 g, 0.20 mmol), and P(o-tol)3 (0.24 g, 0.79 mmol) were combined in a 50 mL Schlenk flask. After the system was placed under vacuum and backfilled with argon three times, dry toluene (15 mL) was injected. The reaction was heated at 105° C. overnight, and then cooled to room temperature. The solvent was removed by a rotary evaporator, and the resulting residue was purified on a silica gel column with hexane/dichloromethane (v/v, 3/1) as the eluent. Recrystallization from a mixture of isopropanol and methanol produced an orange crystalline product (1.81 g, 72.7%).

5-chloro-4-(4-dodecylthiophen-2-yl)-7-(thiophen-2-yl) benzo[c][1,2,5]thiadiazole (1.81 g, 3.60 mmol) was added to a 100 mL Schlenk flask, followed by anhydrous THF (60 mL). The solution was cooled to −78° C. before N-bromosuccinimide (1.34 g, 7.55 mmol) was added in portions. The reaction was gradually warmed to room temperature and stirred overnight. The reaction was stopped by adding saturated potassium carbonate solution and then extracted with hexane. The combined organic layers were dried over anhydrous MgSO4. After the removal of solvent, the resulting mixture was subjected to column purification with hexane as the eluent. Red crystal (2.0 g, 81.7%) was obtained as product after recrystallization in isopropanol and drying in vacuo.

Figure 20:
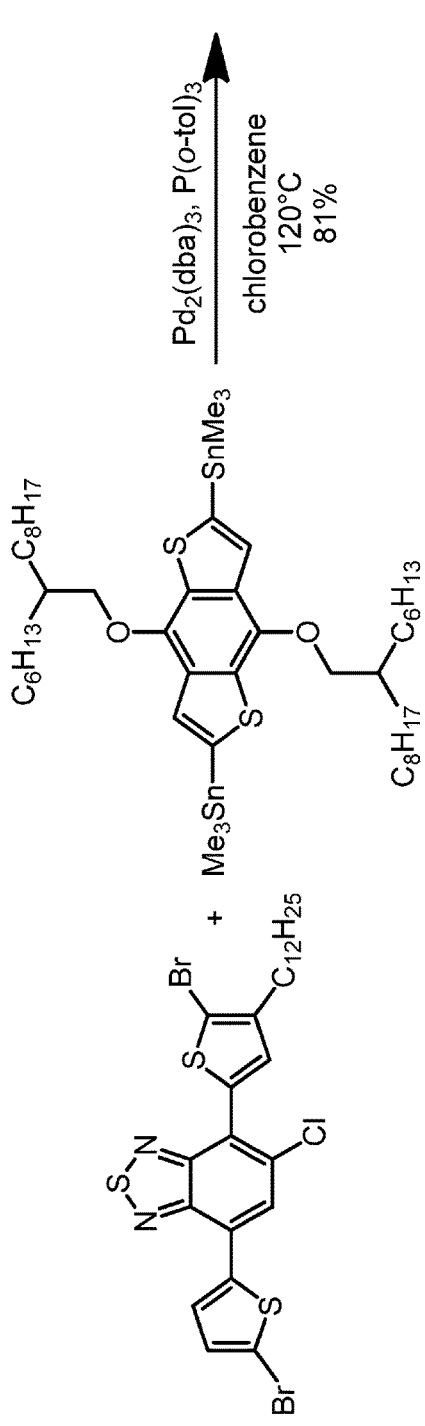
FIG. 20, depicts the reaction of Example 6.
Figure 20:
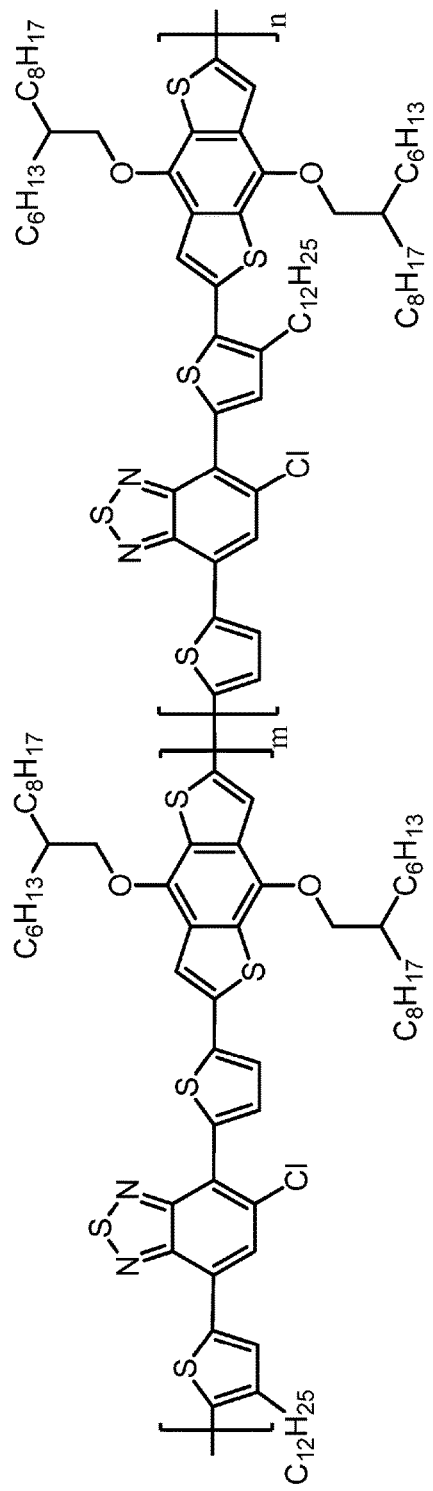

In a Schlenk flask, 4-(5-bromo-4-dodecylthiophen-2-yl)-7-(5-bromothiophen-2-yl)-5-chlorobenzo[c][1,2,5]thiadiazole (72.9 mg, 0.11 mmol), 4,8-Bis[(2-hexyldecyl)oxy]-2,6-bis(1,1,1-trimethylstannanyl)benzo[1,2-b:4,5-b']dithiophene (110 mg, 0.11 mmol), P(o-tol)$_3$ (5.4 mg, 0.018 mmol), and Pd$_2$(dba)$_3$ (2.6 mg, 2.9 μmol) were combined and degassed for 30 min. After refilling with argon, dry chlorobenzene (1.8 mL) was added. Two freeze-pump-thaw cycles were performed, and the reaction was heated to 120° C. for 24 hours. After cooling to room temperature, the polymer was precipitated in MeOH, and the crude polymer was purified by Soxhlet extraction, washing sequentially with acetone, hexanes, and chloroform. The polymer, Example 6 (85 mg, 81%), was recovered in the chloroform fraction. The polymer is depicted in FIG. 20.

Device Fabrication

The photoactive layer consisted of the donor polymer and acceptor PCBM at a ratio of 1:1.2, respectively. The total solution concentration ranged from 36 to 14 mg/mL in 1:1 o-dichlorobenzene and chlorobenzene. The photoactive layer solution was stirred and heated at 80° C. overnight in a nitrogen filled glove box. The next day, 3 vol % of 1,8-diiodooctane (DIO) was added and the solution was heated on the hot plate at 80° C. for an hour. The solution was then filtered with a 2.7 μm glass fiber syringe filter.

Indium tin oxide (ITO) patterned glass substrates were cleaned by successive 15 min ultra-sonications in detergent, deionized water, acetone, and isopropanol. The freshly cleaned substrates were left to dry overnight at 80° C. Preceding fabrication, the substrates were further cleaned for 1 min in a UV-ozone chamber and the electron transport layer, zinc tin oxide:fullerene, was immediately spin coated on top.

Single component or mixed metal oxide solutions were filtered directly onto ITO with a 0.25 μm poly(tetrafluoroethylene) filter and spin cast at 4000 rpm for 40 seconds. Films were then annealed at 210° C. for 15 min, and directly transferred into a nitrogen filled glove box.

The photoactive layer was deposited from a 110° C. solution onto ITO/ZTO:PCBNOH substrates also at 110° C. The photoactive layer was spin cast at 600 rpm for 40 seconds and 1200 rpm for 2 seconds and directly transferred into a glass petri dish to solvent anneal for 18+ h. Some devices were thermally annealed on a hot plate after drying for 18+ h. After solvent annealing, the substrates were loaded into the vacuum evaporator where MoO$_x$ (hole transport layer) and Ag (anode) were sequentially deposited by thermal evaporation. Deposition occurred at a pressure of 1×10$^{-6}$ torr. MoO$_x$ and Ag had thicknesses of 3.5 nm and 120 nm, respectively. The deposition rate for the MoO$_x$ was 0.6-1 Å/s and Ag was 1.5-2 Å/s. Samples were then encapsulated with glass using an epoxy binder and treated with UV light for 3 min.

Device Testing

Devices with an active area of 0.08306 cm$^2$ were tested under AM 1.5G 100 mW/cm$^2$ conditions with a Newport Thermal Oriel 91192 1000 W solar simulator (4"×4" illumination size). The current density—voltage curves were measured using a Keithley 2400 source meter. The light intensity was calibrated with a crystalline silicon reference photovoltaic (area=0.4957 cm$^2$) fitted with a KG-5 filter (calibrated by the Newport to minimize spectral mismatch).

Figure 21:
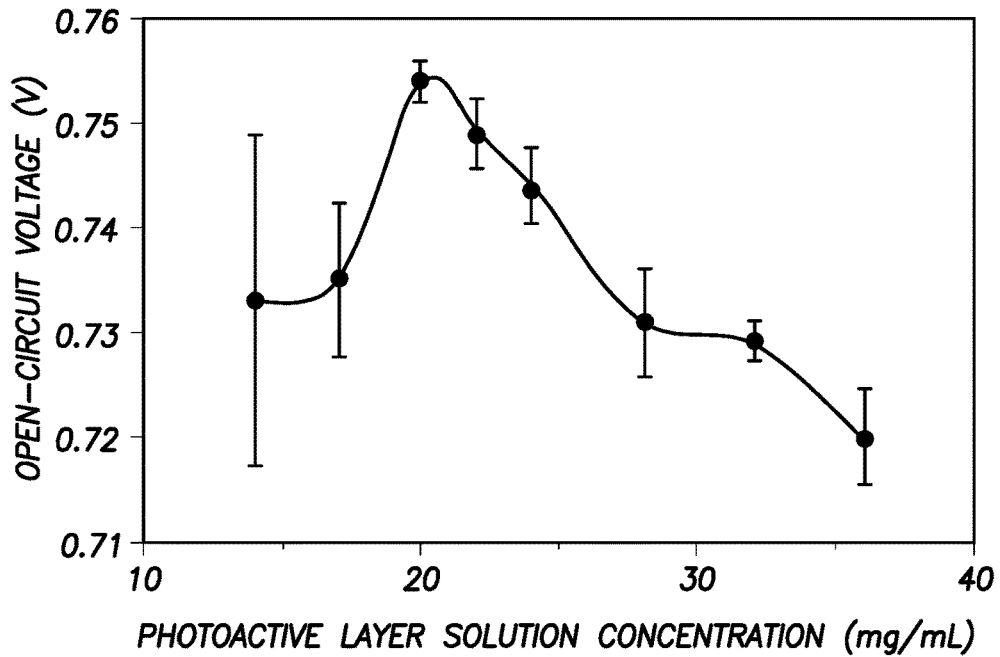
FIG. 21, depicts the effect of the casting solution concentration on Example 6 on the open-circuit voltage of an organic photovoltaic device.

FIG. 21 depicts the effect of the casting solution concentration on Example 6 on the open-circuit voltage of an organic photovoltaic device.

Figure 22:
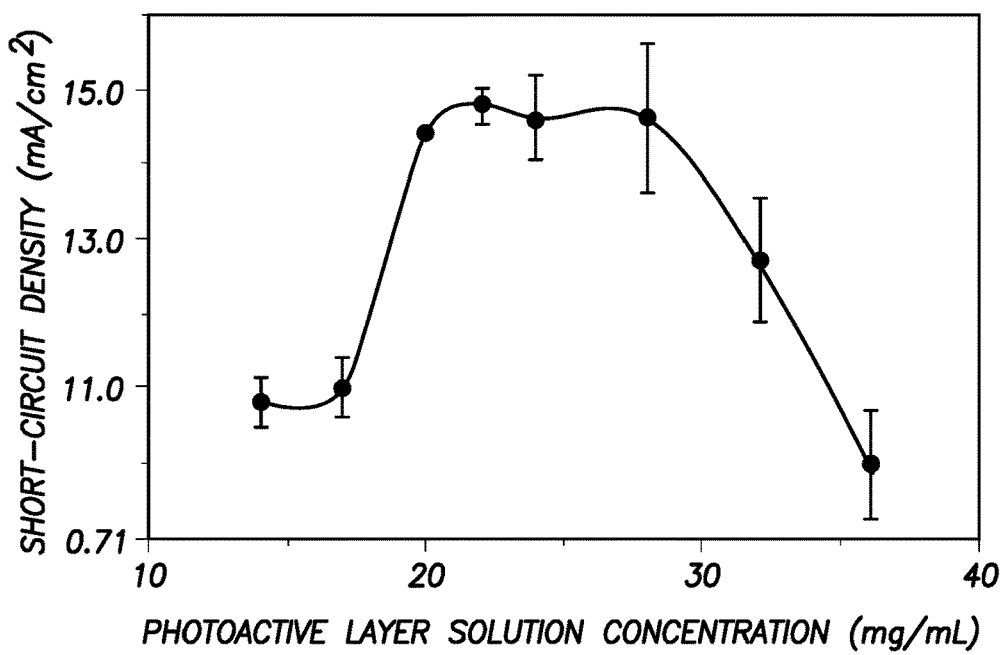
FIG. 22, depicts the effect of the casting solution concentration on Example 6 on the short-circuit current density of an organic photovoltaic device.

FIG. 22 depicts the effect of the casting solution concentration on Example 6 on the short-circuit current density of an organic photovoltaic device.

Figure 23:
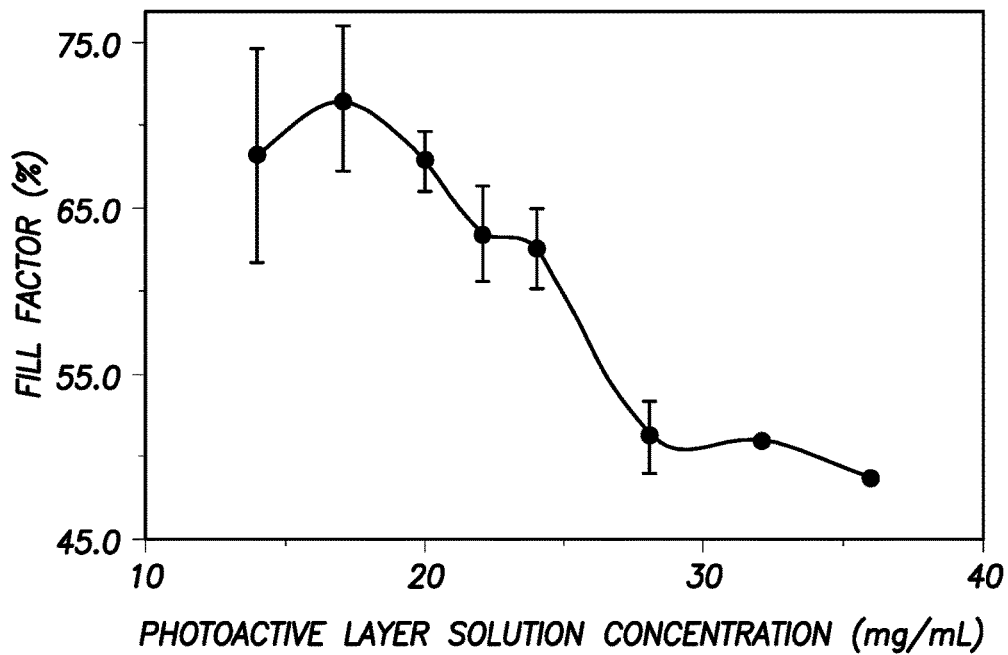
FIG. 23, depicts the effect of the casting solution concentration on Example 6 on the fill factor of an organic photovoltaic device.

FIG. 23 depicts the effect of the casting solution concentration on Example 6 on the fill factor of an organic photovoltaic device.

Figure 24:
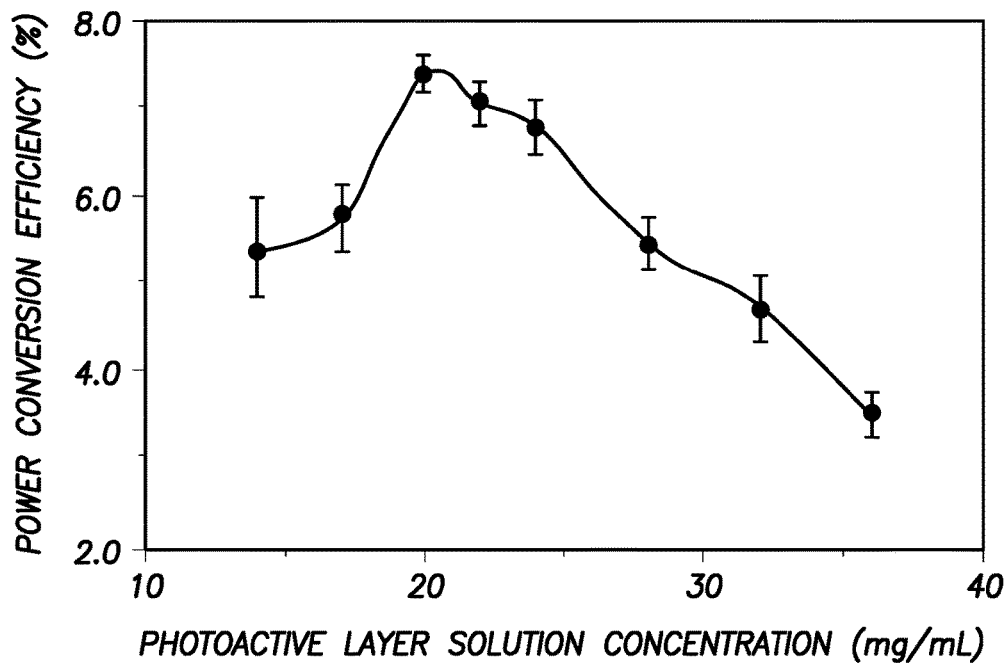
FIG. 24, depicts the effect of the casting solution concentration on Example 6 on the power conversion efficiency of an organic photovoltaic device.

FIG. 24 depicts the effect of the casting solution concentration on Example 6 on the power conversion efficiency of an organic photovoltaic device.

Figure 25:
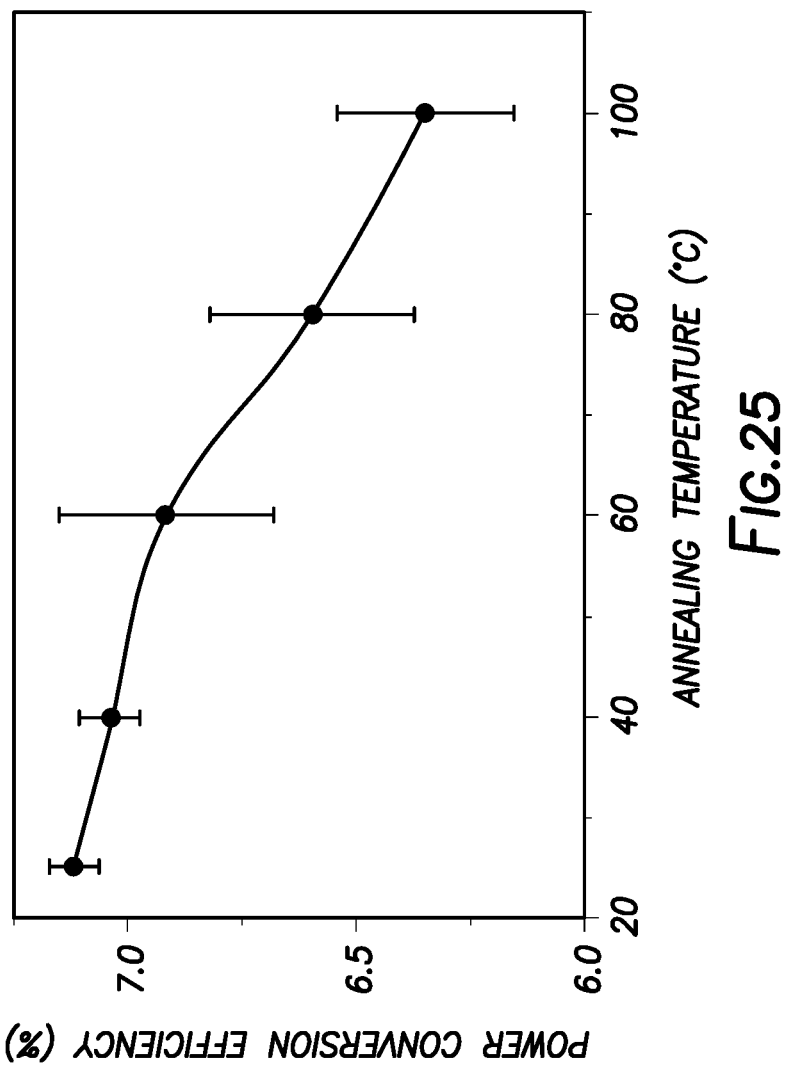
FIG. 25, depicts the effect of the annealing temperature concentration on Example 6 of an organic photovoltaic device.

FIG. 25 depicts the effect of the annealing temperature concentration on Example 6 of an organic photovoltaic device.

The device parameters of Example 6 on different casting solution concentrations are listed below in Table 2.

TABLE 2

| Concentration (mg/mL) | Voc (V) | Jsc (mA/cm$^2$) | Fill Factor % | Power Conversion Efficiency % |
|---|---|---|---|---|
| 14 | 0.75 | 11.3 | 76 | 6.2 |
| 17 | 0.741 | 11.6 | 76 | 6.2 |
| 20 | 0.756 | 14.7 | 70 | 7.6 |
| 22 | 0.754 | 15.1 | 67 | 7.4 |
| 24 | 0.750 | 15.2 | 67 | 7.2 |
| 28 | 0.737 | 16 | 54 | 5.9 |
| 32 | 0.732 | 14.0 | 51.9 | 5.3 |
| 36 | 0.727 | 11.1 | 49.5 | 4.0 |

The device parameters of Example 6 on different annealing temperatures are listed below in Table 3.

TABLE 3

| Annealing Temperature (° C.) | Voc (V) | Jsc (mA/cm$^2$) | Fill Factor % | Power Conversion Efficiency % |
|---|---|---|---|---|
| 25 | 0.741 | 13.7 | 71.9 | 7.18 |
| 40 | 0.745 | 14.8 | 73 | 7.15 |
| 60 | 0.944 | 14.4 | 70 | 7.2 |
| 80 | 0.752 | 13.0 | 74 | 6.9 |
| 100 | 0.759 | 12.1 | 74 | 6.6 |

In closing, it should be noted that the discussion of any reference is not an admission that it is prior art to the present invention, especially any reference that may have a publication date after the priority date of this application. At the same time, each and every claim below is hereby incorporated into this detailed description or specification as an additional embodiment of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:
1. A molecular complex comprising:

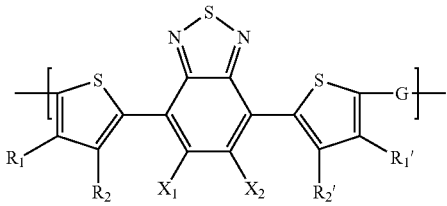

wherein:
X1 and X2 are independently selected from the group consisting of: H, Cl, F, CN, alkyl, alkoxy, ester, ketone, amide and aryl groups;
R1, R2, R1' and R2' are side chains independently selected from the group consisting of:
H, Cl, F, CN, alkyl, alkoxy, alkylthio, ester, ketone and aryl groups and wherein R2 and R2' are not identical;
G is an aryl group; and
wherein the thiophene groups are unsymmetrical and wherein the molecular complex is part of a polymer with a molecular weight ranging from about 1,000 to about 100,000 kDa.

2. The molecular complex of claim 1, wherein the molecular complex is used as photovoltaic material in one or more photovoltaic devices.

3. The molecular complex of claim 2, wherein the one or more photovoltaic devices are polymer solar cell devices or photodetector devices.

4. The molecular complex of claim 1, wherein the molecular complex is used as an active layer material in one or more electronic devices.

5. The molecular complex of claim 4, wherein the one or more electronic devices are field effect transistors, light emitting devices and sensors, electrochromic devices and capacitors.

6. The molecular complex of claim 1, wherein when used as a photovoltaic polymer produces a power conversion efficiency greater than 7.0%.

7. The molecular complex of claim 1, wherein when used as a photovoltaic polymer produces a fill factor greater than 69%.

8. The molecular complex of claim 1, wherein R1 and R1' are not identical.

* * * * *